US006711424B1

(12) United States Patent
Fine et al.

(10) Patent No.: US 6,711,424 B1
(45) Date of Patent: Mar. 23, 2004

(54) METHOD OF OPTICAL MEASUREMENT FOR DETERMING VARIOUS PARAMETERS OF THE PATIENT'S BLOOD

(75) Inventors: Ilya Fine, Rehovot (IL); Leonid Shvartsman, Jerusalem (IL)

(73) Assignee: Orsense Ltd., Rehovot (IL)

( * ) Notice: Subject to any disclaimer, the term of this patent is extended or adjusted under 35 U.S.C. 154(b) by 0 days.

(21) Appl. No.: 10/168,951

(22) PCT Filed: Dec. 22, 1999

(86) PCT No.: PCT/IL99/00694

§ 371 (c)(1),
(2), (4) Date: Nov. 5, 2002

(87) PCT Pub. No.: WO01/45553

PCT Pub. Date: Jun. 28, 2001

(51) Int. Cl.⁷ .................................................. A61B 5/00
(52) U.S. Cl. ..................................... 600/322; 600/335
(58) Field of Search ................................ 600/309–310, 600/322–324, 335

(56) References Cited

U.S. PATENT DOCUMENTS

| 4,201,470 A | * | 5/1980 | Ehrly et al. ................... 356/39 |
| 4,463,762 A | | 8/1984 | Rubens |
| 4,822,568 A | * | 4/1989 | Tomita ........................ 356/39 |
| 4,883,055 A | | 11/1989 | Merrick |
| 4,927,264 A | | 5/1990 | Shiga et al. |
| 4,975,581 A | | 12/1990 | Robinson et al. |
| 5,054,487 A | | 10/1991 | Clarke |
| 5,057,695 A | | 10/1991 | Hirao et al. |
| 5,069,214 A | | 12/1991 | Samaras et al. |
| 5,638,816 A | | 6/1997 | Kiani-Azarbayjany et al. |
| 5,810,734 A | * | 9/1998 | Caro et al. .................. 600/485 |
| 5,827,181 A | | 10/1998 | Dias et al. |
| 5,833,602 A | * | 11/1998 | Osemwota ................... 600/310 |
| 5,931,779 A | | 8/1999 | Arakaki et al. |
| 6,178,342 B1 | * | 1/2001 | Borgos et al. ............... 600/322 |
| 6,222,189 B1 | | 4/2001 | Misner et al. |
| 6,400,972 B1 | * | 6/2002 | Fine ............................ 600/322 |

FOREIGN PATENT DOCUMENTS

| WO | WO 98 17174 | 4/1998 |
| WO | WO 99 65384 | 12/1999 |
| WO | WO 00 09004 | 2/2000 |

OTHER PUBLICATIONS

Brinkman et al., Quantitative Evaluation of the Rate of Rouleaux Formation of Erythrocytes by Measuring Light Reflection ("Syllectometry"), (1963), *Proc. Kon. Ned. Akad. Wetensch. Ser. C. Biol. Med. Sci.*, vol. 66, pp. 236–248.

Ishimaru, "Wave Propagation and Scattering in Random Media", *Academic Press, New York*, (1978), vol. 1–2, pp. 23–30, 63–68.

Van De Hulst, "Light Scattering by Small Particles", *Dover Publication, Inc. New York*, (1957), pp. 85–97.

(List continued on next page.)

*Primary Examiner*—Max F. Hindenburg
*Assistant Examiner*—Matthew Kremer
(74) *Attorney, Agent, or Firm*—Browdy and Neimark, P.L.L.C.

(57) ABSTRACT

A method for optical measurements of desired parameters of the patient's blood is presented. A state of the blood flow cessation is provided within a measurement region and maintained during a predetermined time period. Measurement sessions are performed within this predetermined time period. Each measurement session includes at least two measurements with different wavelengths of incident light. Obtained measured data is representative of the time dependence of light response of the blood in the measurement region. The analyses of the measured data enables the determination of the desired blood parameters extracted from optical characteristics associated with the erythrocytes aggregation process during the state of the blood flow cessation.

36 Claims, 10 Drawing Sheets

OTHER PUBLICATIONS

Twersky, "Interface Effects in Multiply Scattering by Large, Low–Refracting, Absorbing Particles", *Journal of the Optical Society of America*, (1970), vol. 60, No. 7, pp. 908–914.

Hemenger, "Optical Properties of Turbid Media with Specularly Reflecting Boundaries: Application to Biological Problems", *Applied Optics*, (1977), vol. 16, No. 7, pp. 2007–2012.

Rogozkin et al., "Long–range Intensity Correlations in Wave Reflection from a Disordered Medium", *Physical Review B.*, (1995), vol. 51, No. 18, pp. 12256–12267.

Rogozkin, "Long–range Intensity Correlations for the Multiple Scattering of Waves in Unordered Media", *JEPT*, (1997), vol. 84, No. 5, pp. 916–939.

Rogozkin et al., "Intensity Correlation in a Disordered Medium with large Scatters", *Physics Letters A*, (1993), vol. 178, pp. 431–439.

Steinke et al., "Role of Light Scattering in Spectrophotometric Measurements of Arteriovenous Oxygen Difference", *IEEE Transactions on Biomedical Engineering*, (1986), vol. BME–33, No. 8, pp. 729–734.

* cited by examiner

METHOD OF OPTICAL MEASUREMENT FOR DETERMINING VARIOUS PARAMETERS OF THE PATIENT'S BLOOD

FIELD OF THE INVENTION

This invention is in the field of optical measuring techniques and relates to a method for determining desired parameters of the patient's blood, for example, the concentration of a substance in blood, such as glucose, hemoglobin, drugs or cholesterol, or other important blood parameters such as oxygen saturation. The invention is particularly useful for non-invasive measurements.

BACKGROUND OF THE INVENTION

Optical methods of determining the chemical composition of blood are typically based on spectrophotometric measurements enabling the indication of the presence of various blood constituents based on known spectral behaviors of these constituents. These spectrophotometric measurements may be effected either in vitro or in vivo. The measurements in vitro are invasive, i.e. require a blood sample to be physically withdrawn and examined. At present, these measurements have become unpopular, due to the increasing danger of infection.

The non-invasive optical measurements in vivo may be briefly divided into two main groups based on different methodological concepts. The first group represents a so-called "DC measurement technique", and the second group is called "AC measurement technique".

According to the DC measurement technique, any desired location of a blood perfused tissue is illuminated by the light of a predetermined spectral range, and the tissue reflection and/or transmission effect is studied. Although this technique provides a relatively high signal-to-noise ratio, as compared to the AC measurement technique, the results of such measurements depend on all the spectrally active components of the tissue (i.e. skin, blood, muscles, fat, etc.), and therefore need to be further processed to separate the "blood signals" from the detected signals. Moreover, proportions of the known components vary from person to person and from time to time. To resolve this problem, calibration must periodically be provided, which constitutes an invasive blood test and therefore renders the DC technique of optical measurements to be actually invasive.

The AC measurement technique focuses on measuring only the "blood signal" of a blood perfused tissue illuminated by a predetermined range of wavelengths. To this end, what is actually measured is a time-dependent component only of the total light reflection or light transmission signal obtained from the tissue. A typical example of the AC measurement technique is the known method of pulse oximetry, wherein a pulsatile component of the optical signal obtained from a blood perfused tissue is utilized for determining arterial blood oxygen saturation. In other words, the difference in light absorption of the tissue measured during the systole and the diastole is considered to be caused by blood that is pumped into the tissue during the systole phase from arterial vessels, and therefore has the same oxygen saturation as in the central arterial vessels.

The major drawback of the AC measurement technique is its relatively low signal-to-noise ratio, especially in cases where an individual has a poor cardiac output, insufficient for providing a pulsatile signal suitable for accurate measurements.

Various methods have been suggested to enhance the natural pulsatile signal of an individual for effecting non-invasive optical measurements, and are disclosed for example in the following patents: U.S. Pat. No. 4,883,055; U.S. Pat. No. 4,927,264; and U.S. Pat. No. 5,638,816. All these techniques utilize the artificially induced volumetric changes of either arterial or venous blood. Since each of these techniques is specific about the kind of blood under test, they all impose severe restrictions on the value of the artificially applied pressure. This is due to different "disturbing pressure values" allowed for different kinds of blood flow. It means that for each kind of blood flow, there is a pressure value that disturbs specifically this kind of flow much more than any other kind. For example, when the artificial pressure at a value of 60 mmHg is applied to a proximal body part, the venous blood flow will be affected, whereas the arterial blood flow will not be affected, since the individual's diastolic pressure is usually higher than 60 mmHg. The applied artificial pressure definitely should not exceed pressures causing substantial deformation of the tissue, since only blood flow changes are supposed to be detected by optical measurements, and the measurements are to be effected in synchronism with the artificial pulse. However, if such an artificially induced pulse causes uncontrollable changes of the optical properties of the tissue, these changes cannot be distinguished from those caused by the blood flow fluctuations which are the target of the measurements.

SUMMARY OF THE INVENTION

There is a need in the art to facilitate the determination of various parameters of the patient's blood, by providing a novel method of optical measurements which can be utilized in a non-invasive manner for in vivo determination of such parameters as the concentration of a substance in blood (e.g., hemoglobin, glucose), oxygen saturation, the difference between the refraction indexes of hemoglobin and plasma in the patient's blood, and/or Erythrocyte Aggregation Rate (EAR).

It is a major feature of the present invention to provide such a method that is universal and does not depend on such conditions as concrete kinetics, aggregation shape, etc. which vary from patient to patient.

The present invention takes advantage of the technique disclosed in the co-pending application assigned to the assignee of the present application. The main idea underlying this technique is based on the fact that the light response characteristics (i.e., absorption and/or scattering) of a blood perfused medium dramatically changes when a character of blood flow changes. It has been found by the inventors, that the optical characteristics of a blood perfused fleshy medium (e.g., the patient's finger) start to change in time, when causing blood flow cessation. In other words, once the blood flow cessation state is established, the optical characteristics start to change dramatically, such that they differ from those of the fleshy medium with a normal blood flow by about 25 to 45%, and sometimes even by 60%. Hence, the accuracy (i.e., signal-to-noise ratio) of the optical measurements can be substantially improved by performing at least two timely separated measurement sessions, each including at least two measurements with different wavelengths of incident radiation.

The main idea of the present invention is based on the investigation that the changes of the light response of a blood perfused fleshy medium at the state of the blood flow cessation (either monotonous or not, depending on the wavelength of incident radiation) are caused by the changes of the shape and average size of the scattering centers in the medium, i.e., red blood cells (RBC) aggregation (Rouleaux effect). The main principles of this effect are disclosed, for example, in the article "Quantitative Evaluation of the Rate of Rouleaux Formation of Erythrocytes by Measuring Light Reflection ("Syllectometry")", R. Brinkman et al., 1963.

At the state of the blood flow cessation, when there is actually no blood flow, no shear forces prevent the erythrocytes' aggregation process. Hence, the light response (transmission) of the blood perfused fleshy medium undergoing the occlusion, which causes the blood flow cessation, can be considered as the time dependence of scattering in a system with growing scatterers.

Generally, light response of a medium is defined by the scattering and absorption properties of the medium. According to the model of the present invention, at the state of blood flow cessation under proper conditions, the crucial parameter defining the time evolution of the light response is a number of erythrocytes in aggregates. Therefore, it can be concluded that the average size of aggregates also changes with time. The scattering properties of blood depend on the size and shape of aggregates (scatterers). As for the absorption properties, they do not depend on the shape and size of scatterers, but depend only on the volume of the components.

Although the time increase of the size of aggregates for a specific patient is unknown, as well as a concrete geometry of aggregates or concrete RBC's refraction index, there exists a parameter, which is universal and does not significantly depend on concrete kinetics, aggregation shape, etc. This parameter is determined as the parametric slope of the line $T_{\lambda 2}(T_{\lambda 1})$ (or $\log T_{\lambda 2}(Log\ T_{\lambda 1})$), wherein $T_{\lambda 2}$ is the time dependence of the transmission of the medium irradiated with the wavelength $\lambda_2$, and $T_{\lambda 1}$ is the time dependence of the transmission of the medium irradiated with the wavelength $\lambda_1$. This enables the explicit usage of the size of aggregates (i.e., the values that are unknown in experiments in vivo) to be eliminated. The time period considered in the determination of the parametric slope may be the so-called "initial time interval" of the entire time period during which the measurements were made at the blood flow cessation state, or the so-called "asymptotic time interval" that follows the initial time interval. The initial time interval is distinguished from the asymptotic time interval, in that the transmission signals more strongly change with time during this interval, as compared to that of the asymptotic time interval.

To determine the parametric slope aimed at determining a desired parameter of blood, the two wavelengths are selected in accordance with the parameter to be determined. For example, if the hemoglobin concentration is to be determined, the selected wavelengths are in those ranges, where the absorption properties of the hemoglobin and plasma are more sharply expressed, namely, the ranges of 600–1000 nm and 1100–1400 nm. If the oxygen saturation is to be determined, the selected wavelengths lie in the ranges where the difference in the absorption of hemoglobin (Hb) and oxyhemoglobin (HbO2) are more sharply expressed, namely, the ranges of 600–780 nm (HbO2 sensitive range) and 820–980 nm (Hb sensitive range). When dealing with the glucose concentration, the spectral ranges of 1500–1600 nm may be added to the above-mentioned range of 600–1300 nm for selecting the two wavelengths, respectively.

Having determined the parametric slope for a specific patient, a corresponding calibration curve presenting the corresponding parametric slope as the function of the desired parameter is used for determining the desired parameter for the specific patient. The calibration curve, or a set of such curves for different parameters, is previously prepared and stored as reference data. The calibration curve is prepared by applying measurements of the present invention and the conventional ones to different patients, and determining the parametric slope and the desired parameter, respectively. For the determination of oxygen saturation, generally, a calibration curve may be prepared by applying measurements of the present invention to a specific patient, but at the multiple-occlusion mode at the blood flow cessation state in a breath hold experiment.

Additionally, it was found that for one wavelength of the incident radiation the time dependence of transmission signal, i.e., T(t), asymptotically falls, and for the another wavelength it grows. This fact allows for constructing a certain rouleaux geometry factor (RGF). This RGF essentially involves the different time evolutions of light responses at the different wavelengths of incident radiation, and may serve as one of the key-parameters for attributing the measurement results to the certain calibration curve.

The RGF may be constructed in different ways. For example, the RGF can be taken as a certain "cut-off" wavelength $\lambda_0$ corresponding to the transmission value staying nearly constant with time. This cut-off wavelength can be determined as the wavelength corresponding to the condition $\Delta T/\Delta t=0$ (or $\Delta(\log T)/\Delta t=0$). On the other hand, it is known from literature and is theoretically obtainable, that a function $K(x(n_{Hb}-n_{pl}))$, which describes the effects of light diffraction on particles depending on the model used, has several extremum values. Here, $x=2\pi a/\lambda$, a being the erythrocyte size; $n_{Hb}$ is the refraction index of hemoglobin and $n_{pl}$ is the refraction index of liquid surroundings, i.e., plasma, which is similar to water by its optical characteristics. It is also known, and is shown in the description below, that the transmission signal is almost proportional to this function K. It is thus evident that the existence of extremum values of the function K is the physical reason for the cut-off wavelengths appearing. Having determined this cut-off wavelength $\lambda_0$, the scattering function $K(x(n_{Hb}-n_{pl}))$ in the particular case (or another relevant diffraction related function) can be used for determining a corresponding value of the parameter as $x(n_{Hb}-n_{pl})$ and the difference $(n_{Hb}-n_{pl})$ for a specific patient.

Indeed, since the erythrocyte size, a, and the difference $(n_{Hb}-n_{pl})$ lie in certain accepted ranges, the ranges for the product $x(n_{Hb}-n_{pl})$ can be defined. The extremum value of the function K corresponds to a certain value of this product, and to the cut-off wavelength $\lambda_0$ which can be determined as described above. Considering that erythrocyte is a biconcave disk or spheroid having its small and long sizes, and that during the aggregation process the erythrocytes adhere to each other along their long surfaces (or in different geometries), at the asymptotic time interval, the actual aggregate size contributing to the scattering after the averaging is equal to the effective transverse size of the aggregate, which in the particular case may be taken, for example, of the order of small size a of the single erythrocyte.

Another example of the RGF may be such a wavelength, $\lambda_{max}$, that corresponds to such a condition that the ratio $\Delta(\log T)/\Delta t$ as the function of wavelength $\lambda$ has its maximal value. This enables to provide an additional calibration parameter, which is specific for a certain blood condition of a specific patient. Other peculiarities, well defined mathematically, of the ratio $\Delta(\log T)/\Delta t$ as the function of wavelength and/or time t enable to characterize the blood conditions of a specific patient, which can be utilized for calibration purposes.

Hence, the knowledge of the RGB for a specific patient enables the determination of the difference $(n_{Hb}-n_{pl})$ for this patient. The knowledge of this data is very important for diagnostic purposes. For example, it is known that the concentration of glucose affects the difference $(n_{Hb}-n_{H2O})$. Furthermore, numerous sets of calibration curves can be prepared, wherein each such set corresponds to a certain value of the RGB, and each calibration curve in the set corresponds to a certain blood parameter. This enables to obtain more precise information about the patient's blood.

Generally speaking, the present invention presents a technique for obtaining and analyzing the time changes of the spectral dependence of the light response (transmission) of the patient's blood at the state of blood flow cessation, wherein these changes result from the effect of scattering on particles of different size (erythrocyte aggregates). The state of blood flow cessation is preferably obtained in vivo by applying over-systolic pressure to the patient's blood perfused fleshy medium, e.g., his finger, but can also be obtained in vitro, by providing the flow of the patient's blood sample into a cuvette and occluding the flow for a certain time period.

For the calculation of the optical properties of blood (reflection and transmission coefficients), properties of the entire system should be connected with the scattering and absorption properties of the unit of the system volume. To this end, the scattering and absorption coefficients are evaluated. As indicated above, for blood, the absorption coefficient $\mu_{abs}$ does not depend on the shape of particles and is their sizes. What does depend on the particle size is the scattering coefficient $\mu_{scat}$. This conclusion is true for various models of multiple scattering theories, such as the model of Twersky, diffusion models, model of Hemenger, model of Rogozkin, and Small-Angle model.

There is thus provided according to one aspect of the present invention, a method of optical measurements of at least one desired parameter of a patient's blood, the method comprising the steps of:
  providing a state of blood flow cessation of the patient's blood within a measurement region, and maintaining the blood-flow cessation state during a predetermined time period;
  performing measurement sessions within said predetermined time period, each measurement session including at least two measurements with different wavelengths of incident light, and obtaining measured data representative of the time dependence of light response of the blood in the measurement region;
  analyzing the measured data for determining said at least one desired parameter, extracted from optical characteristics associated with erythrocytes aggregation process during the state of the blood flow cessation.

The term "measurement sessions" used herein signifies either timely separated measurements, or continuous measurements over a certain time interval lying within the predetermined time period during which the blood flow cessation state is maintained.

The state of blood flow cessation can be provided by occluding the blood flow within a measurement region of the patient's blood perfused fleshy medium, by applying over systolic pressure to the medium. In this case, the pressure is applied at a first location on the patient's organ, while measurements are applied to a second location downstream of the first location with respect to the direction of normal blood flow. In this case, the measurements start upon detecting the existence of the blood flow cessation state, through preliminary optical measurements. Occlusion is maintained during a predetermined period of time insufficient for irreversible changes in the fleshy medium, ranging generally from one second to several minutes. However, the same measurements can be applied to the patient's blood sample in a cuvette.

The analysis of the measured data may include the determination of a parametric slope for the specific patient, in which case certain reference data is utilized in the form of a calibration curve presenting the parametric slope as a function of values of the desired parameter. For the purposes of this specific application, the different wavelengths are preferably selected in accordance with the blood parameter to be determined. If the concentration of a substance in the patient's blood is to be determined, the use of two different wavelengths is sufficient.

Alternatively or additionally, the analysis of the measured data includes the determination of an RGF. The term "RGF" used herein is a factor characterizing the light response of blood in the state of blood flow cessation as the function of time and wavelengths of incident radiation, associated with the Rouleaux effect, or erythrocytes' aggregation. In this case, the theoretical data indicative of a scattering function $K(x(n_{Hb}-n_{pl}))$ may be used for determining the parameter $x(n_{Hb}-n_{pl})$ for the specific patient, if the "cut-off" wavelength serves as the RGF. To this end, preferably more than two different wavelengths of incident radiation are used in each measurement session and corresponding time variations of the transmission signals T(t) are measured in order to construct the proper RGF. Then, in the example of the cut-off wavelength, a ratio $\Delta(\log T)/\Delta t$ (or $\Delta T/\Delta t$) as the function of the wavelength $\lambda$ is determined for the time interval $\Delta t$ that lies substantially within the asymptotic time interval. The point $\lambda_0$ corresponding to the condition $\Delta(\log T)/\Delta t=0$ is the cut-off wavelength of incident radiation corresponding to a certain time stable transmission for a specific patient, which, in turn, corresponds to the extremum of the function $K(x(n_{Hb}-n_{pl}))$, within the accepted range of $(x(n_{Hb}-n_{pl}))$.

Another important parameter that can be obtained through the analysis of the measured data is the EAR, which is determined as the ratio $\Delta T/\Delta t$ or $\Delta(\log T)/\Delta t$. Generally, the use of only one wavelength of incident radiation is sufficient for this specific application. But practically, in order to enable the determination of several different parameters through the single measurement procedure, more than one wavelength is used.

According to another broad aspect of the present invention, there is provided a method of optical measurements of desired parameters of a patient's blood extracted from optical characteristics associated with erythrocytes aggregation process during the state of the blood flow cessation, the method comprising the steps of:
  providing the state of the blood flow cessation within a measurement region, and maintaining the blood-flow cessation state during a predetermined time period;
  performing measurement sessions within said predetermined time period, each measurement session including at least two measurements with different wavelengths of incident light, and obtaining measured data representative of the time dependence of light response of the blood in the measurement region;
  analyzing the measured data for determining said at least one desired parameter, by determining at least one parametric slope value and a Rouleaux Geometry Factor (RGF) for said patient, the RGF characterizing the changes of the light response of blood at the state of the blood flow cessation as the function of time and wavelengths of the incident radiation, associated with the erythrocytes' aggregation.

According to yet another broad aspect of the present invention, there is provided a method of optical measurements of at least one desired parameter of blood of a specific patient extracted from optical characteristics associated with erythrocytes aggregation process during the state of blood flow cessation, the method comprising the steps of:

providing reference data in the form of a function describing diffraction effects on particles, $K(x(n_{Hb}-n_{H2O})$, wherein $x=2\pi a/\lambda$; a is the size of erythrocyte, $n_{Hb}$ is the refraction index of hemoglobin and $n_{pl}$ is the refraction index of water, $\lambda$ is the wavelength of incident radiation;

providing the state of the blood flow cessation and maintaining said state during a predetermined period of time;

performing measurement sessions within said predetermined time period, each measurement session including several measurements with different wavelengths of incident radiation, and obtaining measured data representative of the time dependence of light response signals;

analyzing the measured data for determining a Rouleaux Geometry Factor (RGF) for the specific patient, the RGF characterizing the changes of the light response of blood at the state of the blood flow cessation as the function of time and wavelengths of the incident radiation, associated with the erythrocytes' aggregation.

According to yet another aspect of the present invention, there is provided a method of optical measurements of at least one desired parameter of blood of a specific patient extracted from optical characteristics associated with erythrocytes aggregation process during the state of blood flow cessation, the method comprising the steps of:

providing reference data in the form of at least one calibration curve corresponding to a parametric slope as a function of values of said desired parameter;

providing the state of the blood flow cessation within a measurement region, and maintaining the blood-flow cessation state during a predetermined time period;

performing timely separated measurement sessions within said predetermined time period, each measurement session including at least two measurements with different wavelengths of incident light, and obtaining the time dependence of transmission signals, wherein the at least two wavelengths are selected in accordance with the desired parameter to be determined;

analyzing the obtained data for determining the parametric slope value for said specific patient;

using said calibration curve for determining the value of said desired parameter for said specific patient.

There is also provided a measurement apparatus for performing non-invasive optical measurements of desired parameters of the patient's blood.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 5a and 5b illustrate the main principles of the determination of a cut-off wavelength, wherein FIG. 5a shows six graphs of the time variations of transmission signals corresponding to six different values of the wavelengths of incident radiation, and FIG. 5b shows a graph of $\Delta(\log T)/\Delta t$ as the function of the wavelength obtained from the graphs in FIG. 5a;

FIGS. 6a and 6b graphically illustrate the main principles of the determination of a parametric slope aimed at determining the concentration of hemoglobin, wherein FIG. 6a illustrates a parametric slope plotted as the transmission logarithm at the wavelength $\lambda_2$, i.e., $\text{Log}(T_2)$, versus the transmission logarithm at the wavelength $\lambda_1$, i.e., $\text{Log}(T_1)$, over the initial time interval, using data from the graphs in FIG. 3a, and FIG. 6b illustrates a calibration curve in the form of the parametric slope as the function of the concentration of hemoglobin.

FIGS. 7a and 7b illustrate the determination of the glucose concentration, wherein FIG. 7a shows the measurement data in the form of transmission signals as the functions of time $T_1(t)$ and $T_2(t)$ for two different wavelengths $\lambda_1$ and $\lambda_2$ of incident radiation, and FIG. 7b shows a parametric slope plotted as the transmission logarithm at the wavelength $\lambda_2$, i.e., $\text{Log}(T_2)$, versus the transmission logarithm at the wavelength $\lambda_1$, i.e., $\text{Log}(T_1)$;

FIGS. 8a to 8c illustrate the determination of the oxygen saturation parameter, wherein FIG. 8a shows two graphs for parametric slopes corresponding to two different pairs of wavelengths, respectively, and FIGS. 8b and 8c illustrate one possible example for plotting a corresponding calibration curve;

DETAILED DESCRIPTION OF THE PREFERRED EMBODIMENTS

A method according to the present invention consists of applying optical measurements to the patient's blood while in the state of blood flow cessation, within a measurement region, by irradiating this region with at least two different wavelengths in the near IR or visible range, and detecting transmission signals as the functions of time during a predetermined time period. This can be implemented by applying over-systolic pressure to a location on the patient's organ so as to create the state of blood flow cessation, and applying the optical measurements to a location on the finger downstream of the pressurized location with respect to the direction of a normal blood flow (in vivo). Alternatively, the flow of a blood sample can be directed into a cuvette, and upon creating the state of blood flow cessation in the cuvette, the optical measurements are applied to the blood sample therein (in vitro).

Figure 1A:
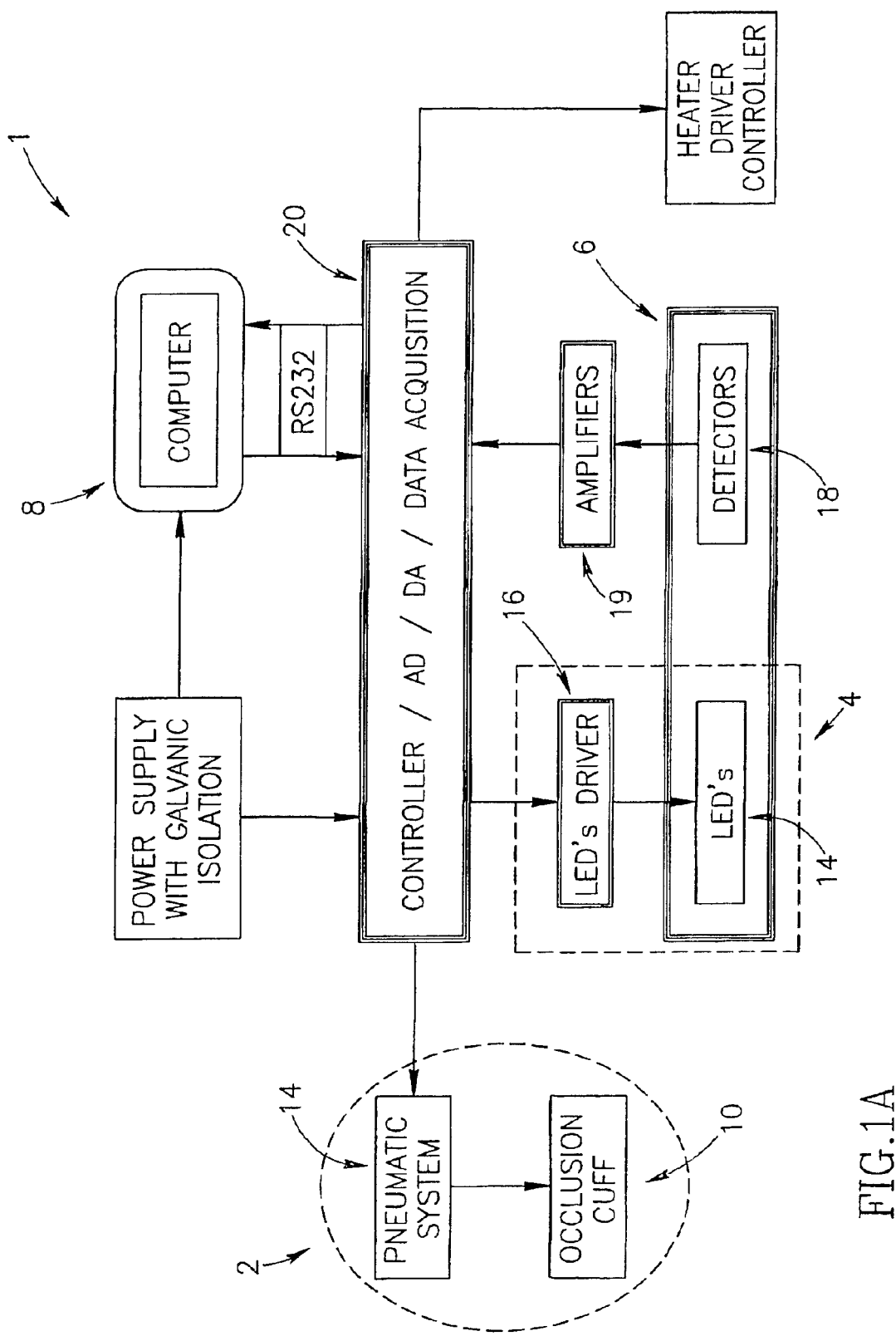
FIG. 1a is a schematic illustration of a measurement apparatus for carrying out a method of the invention applied to the patient's finger for performing non-invasive, in vivo, measurements.

FIG. 1a illustrates a block diagram of a measuring apparatus 1 for carrying out the method of the present invention in a non-invasive manner. The apparatus includes such main constructional parts as a pressurizing assembly 2, an illumination assembly 4, a detection assembly 6, and a control unit 8. The pressurizing assembly 2 is composed of an occlusion cuff 10 which may be of any known suitable type for attaching to the patient's organ, e.g., finger (not shown), and a pneumatic system 12 that applies pressure to the location on the patient's tissue underneath the cuff 10. The illumination assembly 4 includes a plurality (an array) of light sources (e.g., LEDs) 14 associated with a suitable drive mechanism 16. Alternatively, although not specifically shown, a single broad band illuminator can be used. The light sources generate incident radiation propagating through tissue at a measurement location. The detection assembly 6 includes one or more frequency selective detectors 18, e.g., spectrophotometer or photodiodes with frequency selective filters, typically equipped with an amplifying means 19. The detection assembly 6 is accommodated so as to detect light response of the tissue at the measurement location, namely light transmitted through the tissue or light reflected therefrom, as the case may be, and generating data representative thereof. A suitable electronic block 20, typically including an analog to digital (A/D) converter and data acquisition means, processes the generated data. The output of the block 20 is coupled to the control unit 8.

It should be noted that the cuff 10 may be accommodated on the patient's wrist or palm, and the illumination/detection assemblies may be located on the patient's finger. Generally speaking, the first location, to which the pressure is applied, and the second location, to which the measurements are applied, are aligned along the direction of the normal blood flow.

The control unit 8 is interconnected between the illumination and detection assemblies 4 and 6, and is coupled to the pneumatic system 12 (i.e., to the pressurizing assembly). Generally speaking, the control unit 8 is a computer device having such known utilities as a memory, a processor, a synchronizer, a display, etc. The processor is preprogrammed by suitable software capable of analyzing the received output of the detection assembly and determining one or more desired conditions of the patient's blood, as will be described more specifically further below.

Figure 1B:
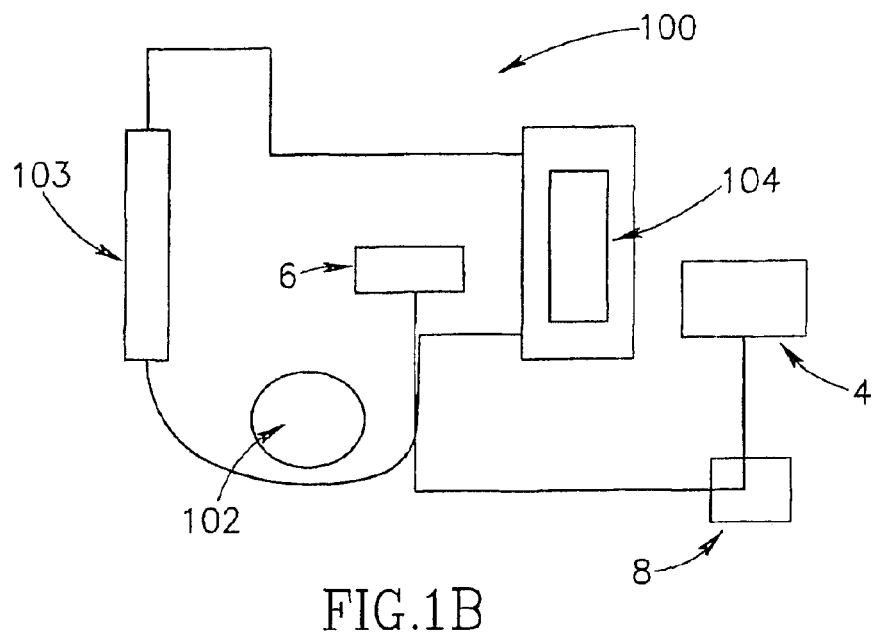
FIG. 1b is a schematic illustration of a measurement apparatus for carrying out a method of the invention applied to a blood sample of the patient's blood in a cuvette for performing invasive, in vitro, measurements.

FIG. 1b illustrates a measurement apparatus 100 utilized for carrying out a method of the present invention in an invasive manner. To facilitate understanding, the same reference numbers are used for identifying those components which are identical in the apparatuses 1 and 100. The apparatus 100 is generally similar to the apparatus 1, having the same illumination and detection assemblies 4 and 6 and the control unit 8. Here, in distinction to the apparatus 1, a pump 102 serves for directing the flow of the patient's blood sample from a buffer 103 into a cuvette 102. By manipulating the pump, the state of blood flow cessation in the cuvette can be provided and maintained for a predetermined period of time.

Figure 2:
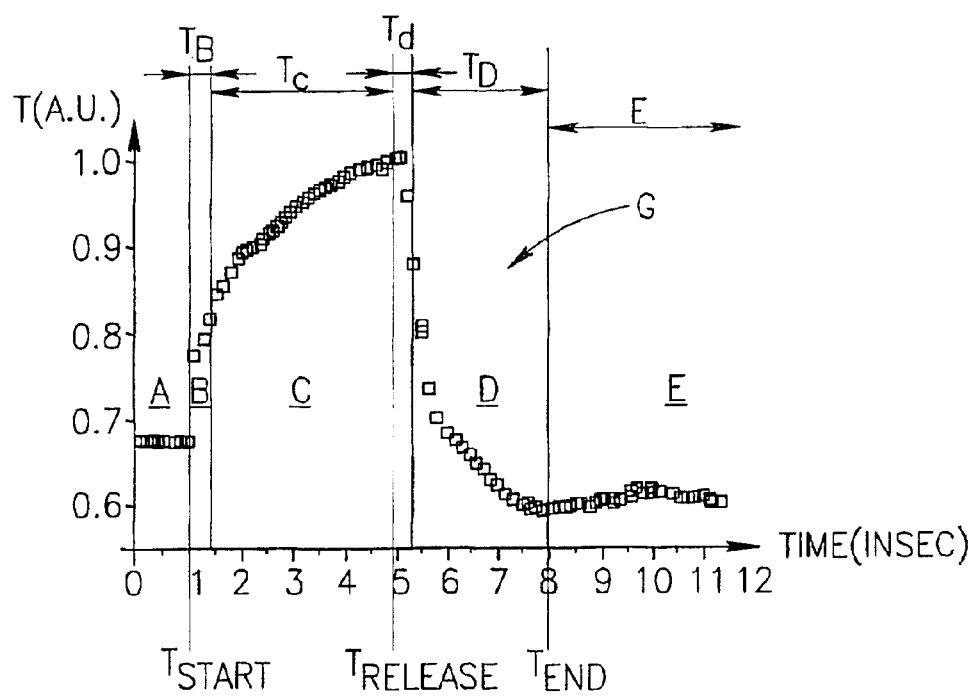
FIG. 2 graphically illustrates the light transmitting characteristic of blood changes under the experimental results obtained by applying the apparatus of FIG. 1a to the patient's blood-perfused fleshy medium, showing the time changes of the blood flow state.

FIG. 2 illustrates a graph G presenting experimental results obtained by applying the apparatuses 1 to the patient's blood perfused fleshy medium. The graph G shows how the light-transmitting characteristic of blood changes under the application of the over-systolic pressure. The transmitting characteristic are shown here as the so-called "Relative Transmission", i.e., in Transmission Arbitrary Units or T(A.U.).

The application of pressure starts at a moment $T_{start}$, and is maintained for a period of time such as not to cause irreversible changes in the fleshy medium (e.g., 4 seconds). The pressure is released at the moment $T_{release}$. Measurements of the Relative Transmission are performed continuously, starting prior to the application of the over-systolic pressure. Different states of the blood flow, designated A, B, C, D and E, are observed. State A is a state of normal blood flow before the over-systolic pressure is applied. As shown, this state is characterized by a standard fluctuating value of the relative light transmission of blood. State B starts at the moment $T_{start}$ (when the pressure is initially applied) and exists during a short period of time $T_B$ (about 0.5 sec) within which the over-systolic pressure is actually applied. Measurements taken during this time period should be disregarded, due to the unavoidable influence of motional and/or other artifacts causing non-monotonic fluctuations of the light transmission.

State C is a state of the temporary cessation of blood flow which lasts within a time period $T_C$ between a moment determined as $(T_{start}+T_B)$ and the moment $T_{release}$. During this period of time, $T_C$, the ascending curve (or descending curve depending on the incident wavelength) of relative light transmission of blood is observed. It reaches its maximum, and may last for about 2–5.5 sec (generally, from one second to several minutes).

It is appreciated that when over-systolic pressure is applied to any proximal part of the body, there is still sufficient space for the redistribution of blood between the exact area of the measurement (i.e. the location of the detector) and the adjacent areas in close proximity to the detector. For example, if the detector is located on a fingertip and over-systolic pressure is applied on the palm, there is enough space between the fingertip and the margin of the applied pressure to "squeeze" the blood from one location to another.

State D is a transitional state of blood flow which takes place after releasing the over-systolic pressure. This state starts with a slight delay $T_d$ (approximately 0.5 sec), i.e. at the moment determined as $(T_{release}+T_d)$. During the time period $T_D$ of the duration of state D, the relative transmission of blood monotonously descends until it reaches values characteristic of the normal blood flow. Such a moment is marked as $T_{end}$ in the drawing. The end of state D, and the beginning of state E, is detected when the changes of the light transmission become periodic and minimal (about 2%). State E is a state of normal blood flow, which is similar to state A.

Figure 3A:
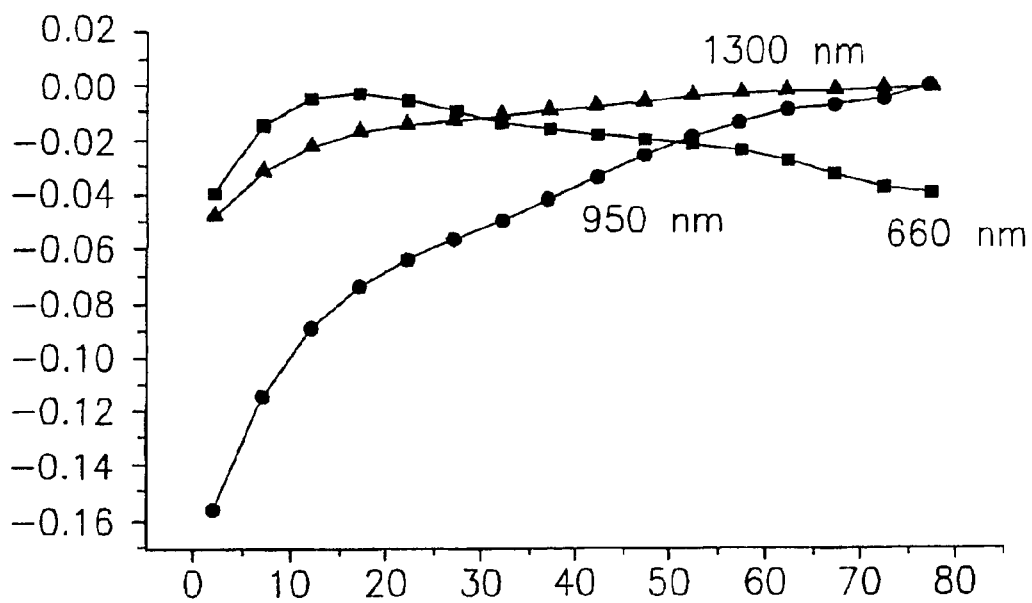
FIGS. 3a and 3b illustrate graphs showing the measured time variations of the transmission signals corresponding to different wavelengths, measured by the to apparatuses of FIGS. 1a and 1b, respectively.
Figure 3B:
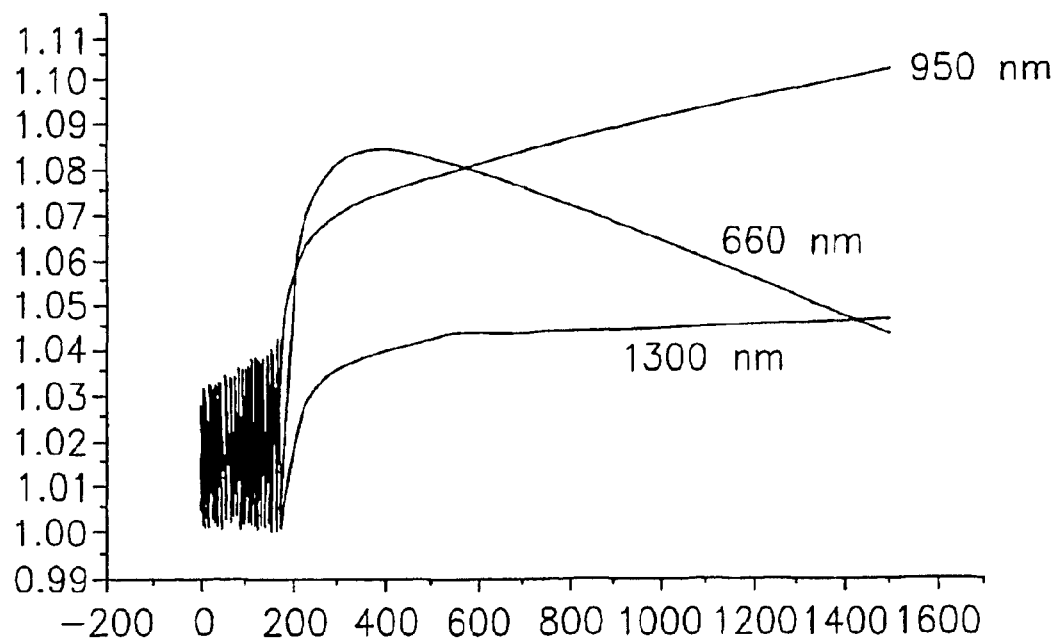

According to the invented method, optical measurements are applied during the state of blood cessation, i.e., state C, with three different wavelengths of incident radiation—$\lambda_1$=660 nm, $\lambda_2$=940 nm and $\lambda_3$=130 nm in the present example, and corresponding transmission signals are measured as the functions of time. FIG. 3a illustrates three graphs showing the measured time variations of the transmission signals, i.e., $T_1(t)$, $T_2(t)$ and $T_3(t)$, corresponding to the wavelengths $\lambda_1$, $\lambda_2$ and $\lambda_3$, respectively, obtained with the apparatus 1 (in vivo). As shown, the transmission always grows during a certain initial time interval $t_{in}$, which is different for different wavelengths of incident radiation, and then, in an asymptotic time interval, $t_{asym}$, it monotonously grows or falls, depending on the wavelength of the incident radiation. FIG. 3b illustrates three graphs corresponding to the time dependence of the transmission signals $T'_1(t)$, $T'_2(t)$ and $T'_3(t)$ obtained with the same three wavelengths, but in vitro, i.e., with the measurement apparatus 100 illustrated in FIG. 1b.

As shown, the corresponding graphs in FIGS. 3a and 3b, i.e., $T_1$ and $T'_1$, $T_2$ and $T'_2$, and $T_3$ and $T'_3$, are similar. This signifies that the same process takes place in the blood while in the patient's body under the occlusion mode, and in the blood, sample in the cuvette, affecting the light response of the blood. This process is the erythrocytes' aggregation.

Turning back to FIG. 2, such an essential difference between the optical characteristics of the blood perfused fleshy medium at the state of blood flow cessation (state C) and those of the fleshy medium with normal blood flow (states A and E) can be explained by the physical and physiological mechanisms—the preferred orientation of red blood cells, their aggregation, and condition of blood vessels. Red blood cells are biconcave discoid cells, the alignment of which drastically changes with the blood flow changes. In turn, scattering properties of the discoid red cells depend on their orientation relatively to the axis of optical measurement. Changes in the scattering properties of the red blood cells alter light absorption of the blood perfused medium. The cessation of the blood flow causes the massive appearance of the aggregated chains that change the light scattering and light absorption of the blood in the fleshy medium. With regard to the condition of blood vessels, the degree of blood perfusion of the vessels and their dimensions essentially depend on the presence of the arterial blood flow, thus affecting optical characteristics thereof.

When radiation propagates in blood or in other biotissues, it is scattered by nonuniformities of the medium which have a random position in space. In a weakly scattering high-transparent medium, radiation undergoes the single scattering by the scatterer and then leaves the system. In another type of medium, defined as the strongly scattering or opaque medium, radiation undergoes many scatterings by the scatterers during the whole time of its propagation in the medium. Blood is the strongly (multiple) scattering medium of this type for near IR and visible spectral ranges.

Generally, the light response of a medium is defined by absorption and scattering affects. Blood consists of particles (erythrocytes) and the surrounding plasma (which is considered to be similar to water by its optical characteristics). Erythrocytes are the concave disks of a certain diameter (about 8 $\mu$m) having a certain volume $V_0$ (about 90 $\mu m^3$). In the entire volume V of blood there are N erythrocytes. The concentration of erythrocytes, $\rho$, is determined as: $\rho = N/V$. The volume per one particle is: $V/N = 1/\rho$, and part of volume that is occupied by erythrocyte is: $H = \rho * V_0$. We have the following condition: $0 \leq H \leq 1$, where $H=0$ stands for no scattering materials in the volume V, and $H=1$ stands for the volume V completely filled with scattering material. Erythrocyte contains a membrane from lipids and some other components, the main one being hemoglobin that occupies 30% of the erythrocyte volume, the plasma (mostly water) occupying the remaining 70% of the erythrocyte volume.

For the calculation of optical properties of blood (reflection and transmission coefficients), properties of the entire system should be connected with the scattering and absorption properties of the unit of the system volume. To this end, the scattering and absorption coefficients have to be evaluated.

The radiation is scattered mainly from erythrocytes. This is associated with the following. As indicated above, plasma is similar to water by its optical characteristics. The refraction index of hemoglobin $n_{Hb}$ is about 1.4 and differs from the refraction index of water, which is $n_{H2O}=1.33$, the relative dielectric constant being $n' = n_{Hb}/n_{H2O} = 1.052$. It is known that the dielectric constant of erythrocyte depends on the dielectric constant of hemoglobin $C_{Hb}$, which changes in the interval 30–36 g/dl. Correspondingly, the relative dielectric constant n' changes in the interval $1.03 < n' < 1.07$ ($1.37 < n_{Hb} < 1.42$). In the whole interval of variation, there is a condition that: $n_{Hb} - n_{pl} << n_{pl}$. Here, the estimations that $n_{Hb} \approx 1.4$, $n_{pl} \approx n_{H2O}$ and $n_{Hb} - n_{H2O} = 1.4 - 1.33 = 0.07$ are taken.

The process that takes place at the state of blood cessation is the aggregation of erythrocytes, during which the erythrocytes forms a long chain. The number of erythrocytes in aggregate depends on many parameters, such as hematocrit H, chemical composition of the blood plasma, and of erythrocyte themselves. Considering that initially the erythrocyte is a concave disk or spheroid having its small size c and the long size a, during the aggregation, the erythrocytes adhere to each other along their long surfaces. If there is aggregation with x erythrocytes, the number of aggregates are N/x. The volume per one aggregate is Vx/N. The volume of one aggregate is $V_0 x$. The part of volume occupied by one aggregate, i.e., the new hematocrit H', is as follows:

$$H' = (Vx/N)*(1/V_0 x) = (V/N*V_0) = H$$

Hence, within this model, the hematocrit of the system does not change in the process of aggregation.

With aggregation, the size of a responding (scattering and absorbing) particle increases. Simulating the aggregates by a sphere, the radius of an aggregate is: $r' = rx^{1/3}$, wherein r is the radius of the erythrocyte. In a spheroid, the small size $c' = cx$ or both sizes c and a are increased, so that: $(a')^2 c' = a^2 cx$.

The total cross-section $\sigma_{tot}$ is equal to the sum of the scattering cross-section $\sigma_{scat}$ and absorption cross-section $\sigma_{abs}$, that is:

$$\sigma_{tot} = \sigma_{scat} + \sigma_{abs}$$

Let us consider the scattering and absorption effects separately:

Scattering Effect

To evaluate the optical properties of the entire system (blood under occlusion or blood sample), the scattering characteristics of a single scatterer should be first evaluated. To this end, WKB approximation is used, which is known in optics as the approximation of anomalous diffraction of Van der Hulst, enabling to obtain a microscopic scattering coefficient of radiation by the erythrocytes of blood. The disclosures in the following articles can be used: "Wave Propagation and Scattering in Random Media", A. Ishimaru, Vol. 1–2, Academic Press, New York, 1978; "Light Scattering by Small Particles" H. C. van der Hulst, Wiley, New York, 1957. In accordance with this approximation, radiation propagates inside the particle in the same direction that the incident radiation does (low-refractive particles), and the radiation wave number inside the particle is equal to the wave number of the radiation in the particle material. The effect of scattering in such a case is connected with the radiation phase change when the radiation propagates inside the particle or more specifically in the hemoglobin of the erythrocyte.

The radiation in visible and near IR region ($\lambda$=0.5–1.6 $\mu$m) is characterized by the following important property: the wavelength of the radiation is smaller than the characteristic size of the particle, that is $\lambda$<r for sphere or $\lambda$<a,c for spheroid. Otherwise, this property is expressed as the inequality: kr=$2\pi r/\lambda$>>1 (or $2\pi a/\lambda$>>1, $2\pi c/\lambda$>1). This inequality is not strong for small erythrocyte size c=1.34 $\mu$m, but is fulfilled with great margin for aggregates of erythrocytes.

The total cross-section of the radiation scattering $\sigma_{scat}$ is equal:

$$\sigma_{scat}=2\cdot Re\int dS(1-e^{2ix'(n'-1)\cos\gamma})=2\cdot Re\int dS(1-e^{2ix(n_{Hb}-n_{pl})\cos\gamma})$$

Here, $\cos\gamma$=l/2r, wherein l is the path length of the radiation ray passing through the scattering sphere; $\gamma$ is the angle between the direction of the radiation propagation and the direction of the radius from the center of the sphere to the first intersection point of the radiation ray with the sphere surface. The parameters x', x and n' are as follows:

$$x' = \frac{2\pi r n_{pl}}{\lambda}; x = \frac{2\pi r}{\lambda}; n' = \frac{n_{Hb}}{n_{pl}}$$

The result is:

$$\sigma_{scat}=4\cdot ReKcom[-2ix(n_{Hb}-n_{pl})]\cdot\pi r^2$$

For real refraction indices ($n_{Hb}$, $n_{pl}$), we have:

$$\sigma_{scat}=2\pi r^2 K[x(n_{Hb}-n_{pl})],$$

wherein $$K(\omega)=1-(\sin(2\omega)/\omega+(\sin(\omega)/\omega)^2;$$

$$\omega=x(n_{Hb}-n_{pl}), x=2\pi r/\lambda.$$

Figure 4A:
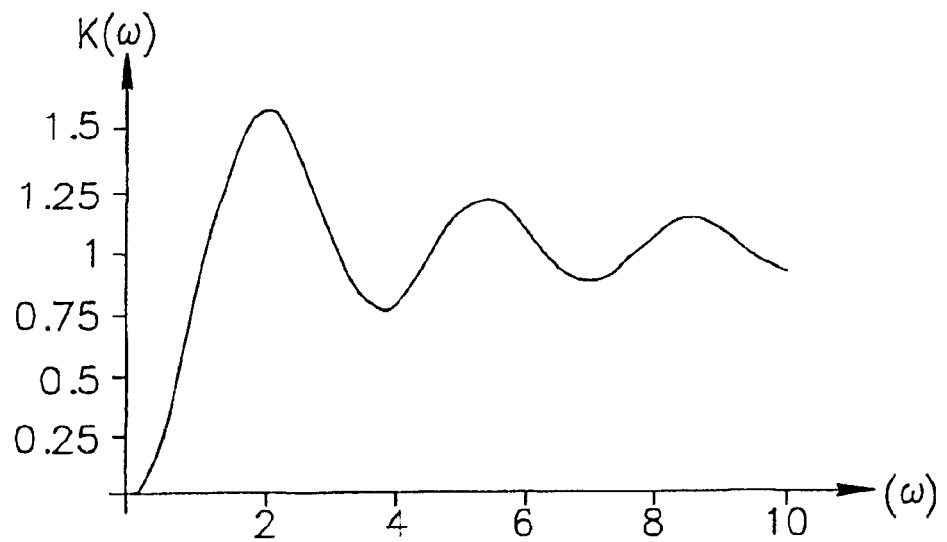
FIGS. 4a and 4b are graphs of the functions $K(\omega)$ and $K(<\omega>)$ describing diffraction effects on particles.

Thus, we defined the function K($\omega$) which is graphically illustrated in FIG. 4a. This function describes diffraction effects on particles depending on the model used. As shown, this function has the asymptotic value 1 at $\omega\to\infty$, in which case $\sigma_{scat}$=$2\pi r^2$. The other asymptotic expression at small $\omega\to 0$, K($\omega$)=$\omega^2$, but this contradicts with the WKB approximation. For blood, there is the intermediate case x$\approx$20 and $\omega\approx$1.

The function K($\omega$) has many maximum and minimum values, the physical sense of which is the interference between the refracted and diffracted waves. Considering the second order statistical correlation of mutual arrangements of the particles, the scattering coefficient $\mu_{scat}$ for spheres may be written as follows:

$$\mu_{scat} = \frac{2\pi r^2}{V_0}K(\omega)\cdot H(1-H)$$

wherein $\omega=2\pi r(n_{Hb}-n_{pl})/\lambda$.

For spheres, the scattering coefficient $\mu_{scat}$ decreases to zero when r increases to infinity. For spheroids, the scattering coefficient $\mu_{scat}$ in WKB approximation depends on the radiation propagation direction, and is as follows:

$$\mu_{scat} = H\cdot(1-H)\cdot(1/V_0)\cdot\sigma_{scat} = 2\cdot\frac{A}{V_0}\cdot H\cdot(1-H)\cdot K(\omega)$$

wherein A is an area of geometrical shadow perpendicular to axes, A=$\pi$I($\zeta$) and I($\zeta$)=[$a^2\cos^2\zeta+c^2\sin^2\zeta$]$^{1/2}$; $\zeta$ is an angle between the axis of spheroid and the direction z of the radiation propagation.

The parameter $\omega$ is as follows.

$$\omega = \frac{4}{3}\cdot\frac{2\pi b}{\lambda}\cdot(n_{Hb}-n_{pl})$$

wherein b is the half the mean thickness of a scatterer (erythrocyte) along the direction of incidence z, that is:

$$b = \frac{3}{4}a\cdot\frac{c}{I(\zeta)} = \frac{3c}{4}\cdot\left(\frac{1}{[1-\varepsilon^2\sin^2\zeta]^{1/2}}\right), \varepsilon^2 = 1-(c/a)^2$$

The scattering coefficient is minimal (b=3c/4) for broadside incidence ($\zeta$=0) and maximal (b=3a/4) for rim-on incidence ($\zeta=\pi/4$).

The similar approach may be applied to each particular geometry of the center of scattering, such as spheroids with averaged parameters over various orientations, etc.

Figure 4B:
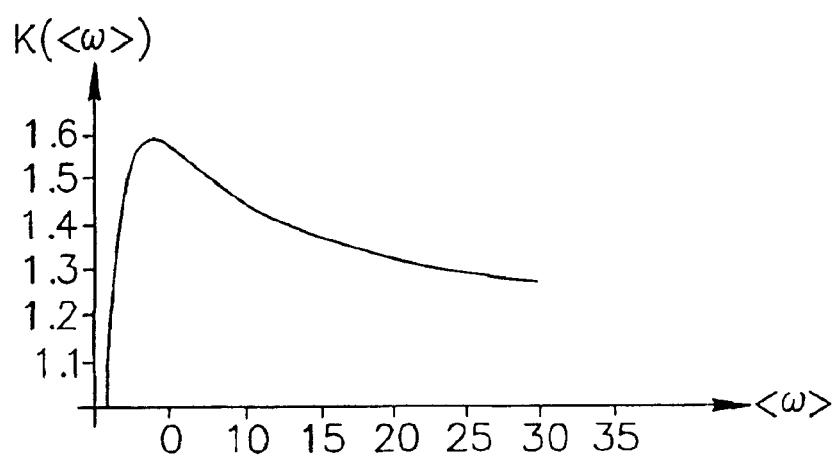

FIG. 4b illustrates the function K(<$\omega$>). It can be seen from this graph that the scattering coefficient $\mu_{scat}$ for spheroids which is proportional to K(<$\omega$>) has the finite limit when one of the sizes c increases to infinity. This limit is determined by the unchanged spheroid size a.

The above equations for the scattering coefficient $\mu_{scat}$ are very important for the evaluation of the optical properties of blood, with taking into account the real size and shape of erythrocytes. This also allows the evaluation of the optical properties of erythrocytes when they aggregate one with another.

Turning back to FIGS. 3a–3b and FIG. 4a, and keeping in mind that $\omega=(2\pi r/\lambda)(n_{Hb}-n_{pl})$, i.e., K is the function of the wavelength $\lambda$ of the incident radiation, we can conclude the following. Since for one wavelength the transmission signal grows with time in the asymptotic time interval $t_{asym}$ and for the other wavelength it falls, there exists such a wavelength (cut-off wavelength) of incident radiation, which causes no time changes in the transmission signal and which corresponds to the extremum (maximum or minimum) of the function K($\omega$). The transmission signal corresponding to the cut-off wavelength of incident radiation will therefore be independent on the erythrocyte aggregation process.

Figure 5A:
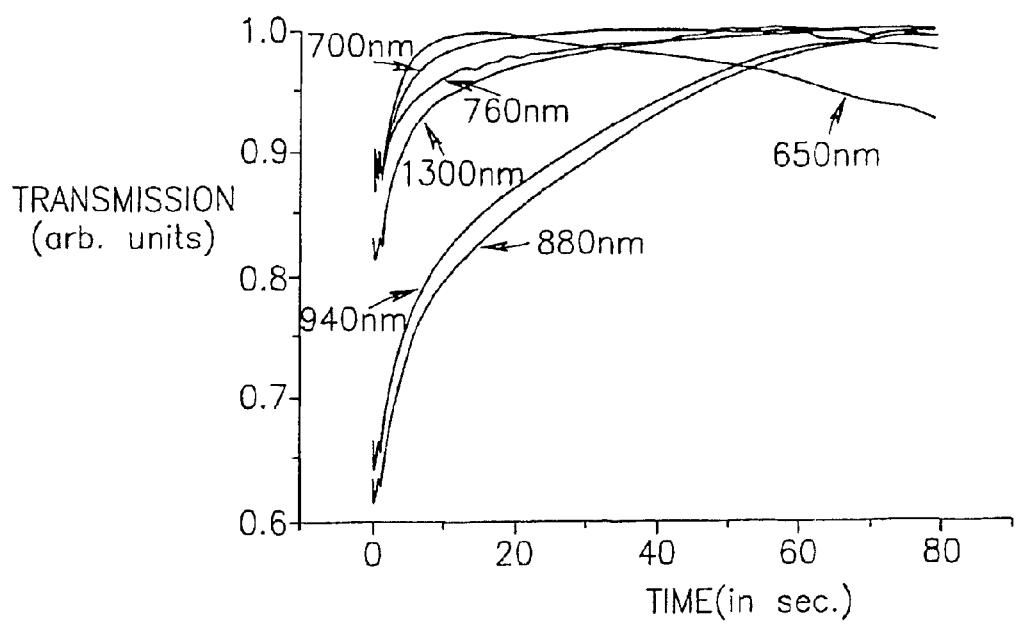
Figure 5B:
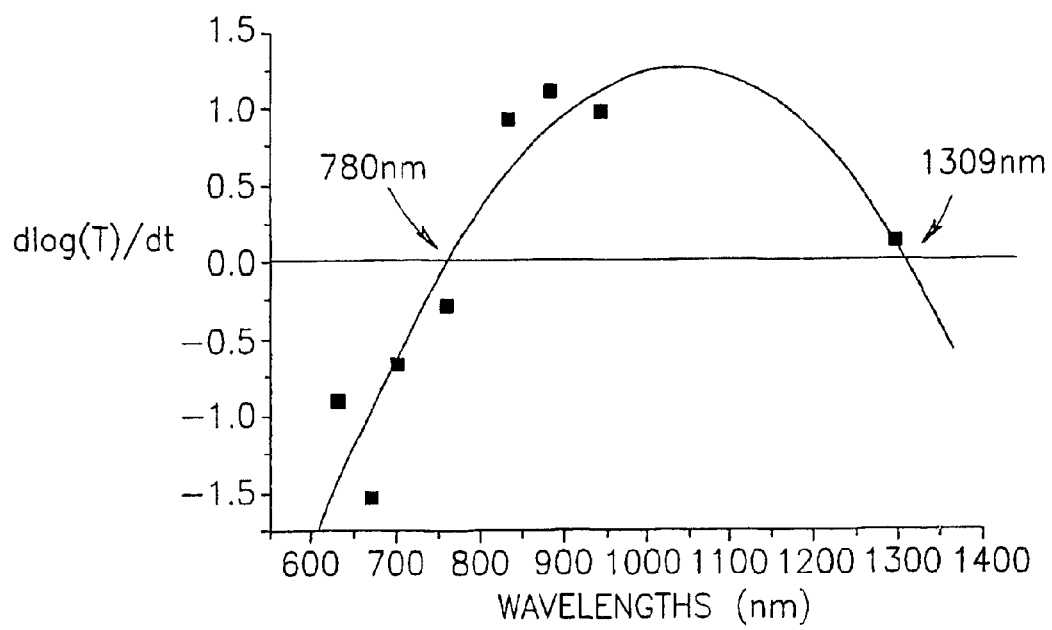

Reference is now made to FIGS. 5a and 5b, illustrating the main principles of the determination of the cut-off wavelength as an example of the particular RGF. FIG. 5a shows the results of in vivo measurements during prolonged occlusion, in the form of several graphs—six in the present example. Graphs $T_1^{\lambda 1}(t)$–$T_6^{\lambda 7}(t)$ of the time variation of transmission signals correspond to different values of the wavelengths of incident radiation: $\lambda_1$=650 nm, $\lambda_2$=700 nm, $\lambda_3$=760 nm, $\lambda_4$=880 nm, $\lambda_5$=940 nm and $\lambda_6$=1300 nm. FIG. 5b shows a graph in the form of a ratio $\Delta(\log T)/\Delta t$ as the function of the wavelength $\lambda$ obtained from the graphs in FIG. 5a, wherein $\Delta t$ lies substantially within the asymptotic time interval $t_{asym}$, where the transmission signals change with time slower than in the initial time interval $t_{in}$. The point $\lambda_0$ is the cut-off wavelength of incident radiation corresponding to a certain time stable transmission for a specific patient, which, in turn, corresponds to the extremum of the function K($\omega$), i.e., its maximum or minimum.

As indicated above, $\omega=x(n_{Hb}-n_{pl})=2\pi r(n_{Hb}-n_{pl})/\lambda$ for the sphere-like erythrocyte, or $\omega=x(n_{Hb}-n_{pl})=2\pi a(n_{Hb}-n_{pl})/\lambda$ for the spheroid-like erythrocyte. For a given cut-off wavelength, $\lambda_0$, the parameter $\omega$ varies from patient to patient, and lies in a certain interval defined by the minimum and maximum acceptable erythrocyte size and minimum and maximal acceptable values of the difference $(n_{Hb}-n_{pl})$. Having determined the wavelength $\lambda_0$ corresponding to the maximum or minimum of $K(\omega)$, and considering the relevant interval of $\omega$ values, the corresponding value of $\omega$ in this interval can be evaluated for the specific patient. This data can be used for further analysis, which will be described further below. As indicated above, the knowledge of the difference $(n_{Hb}-n_{pl})$ is indicative, for example, of the glucose concentration.

Absorption Effect

The incident radiation is absorbed by the blood components—hemoglobin and water. The absorption coefficient of hemoglobin $\mu^{Hb}_{abs}$ (per unit of hemoglobin density) and analogous absorption coefficient of plasma (water) $\mu^{pl}_{abs}$ can be obtained experimentally and are known from literature. These coefficients depend on the wavelength of incident radiation, and their magnitudes may be estimated as follows: $\mu^{Hb}_{abs} \approx 2.5*10^{-2}$ dl/(g*mm) and $\mu^{pl}_{abs} \approx 1.5*10^{-3}$ dl/(g*mm).

The total absorption coefficient is equal:

$$\mu_{abs}=\mu^{Hb}_{abs}\cdot C_{Hb}\cdot H+\mu^{pl}_{abs}\cdot C_{pl}=\mu^{Hb}_{abs}\cdot C_{Hb}\cdot H+\mu^{pl}_{abs}\cdot (100\ g/dl-C_{Hb}\cdot H)$$

Here, $C_{Hb}$ is the concentration of hemoglobin and is approximately equal to 30 g/dl; $\mu^{Hb}_{abs}$ is the absorption coefficient of hemoglobin and is approximately equal to $2.5*10^{-2}$; and $\mu^{pl}_{abs}$ is the absorption coefficient of plasma which is about $1.58*10^{-3}$ (considering that the optical characteristics of plasma as similar to those of water).

Since there is a concrete geometry of erythrocytes in the system, the role of their spherical shape in the absorption of radiation should be considered.

The absorption coefficient is expressed by the imaginary part of the refraction indices and is as follows:

$$\sigma_{abs}=2Re\int dS(1-e^{-4x(s\cdot lmn_{Hb}-1-s)\cdot lmn_{pl})\cos\gamma})=2\cdot Kcom(4x(slmn_{Hb}+(1-s)lmn))$$

wherein hemoglobin occupies only the part s of the erythrocyte volume $V_0$.

For the real system $x\approx 18$, lm $n_{Hb}$,$n_{pl}$ is about $10^{-4}$ and the argument of function is small. Considering the expression for Kcom[y]:

$$Kcom[y]=\frac{y}{3}-\frac{y^2}{8}+\frac{y^3}{30}+\ldots$$

we have:

$$\sigma_{abs}=\frac{8}{3}x\cdot\pi r^2\cdot(s\cdot lmn_{HB}+(1-s)\cdot lmn_{pl})$$

Taking into account the following:

$$\frac{4\pi}{3}\cdot r^3=V_0$$

we receive:

$$\sigma_{abs}=(\mu^{Hb}_a\cdot C_{Hb}+\mu^{pl}_a\cdot(1-s)\cdot\rho_{pl})V_0$$

For the absorption coefficient of erythrocyte we have the expression:

$$\mu_{abs}^{(eryth)}=\rho\cdot\sigma_{abs}=(\mu^{Hb}_{abs}\cdot C_{Hb}\cdot H+\mu^{pl}_{abs}\cdot(1-s)\cdot H\cdot\rho_{pl}$$

It is thus evident that for blood, the absorption coefficient does not depend on the shape of particles and their sizes, but depends only on the volume of the components. With the contribution of water in the space between the erythrocytes, we reproduce again the above, more general equation for $\mu_{abs}$.

For the opposite limit of very large particles, we have: $\sigma_{abs}\approx\pi r^2$, and therefore (when $x(n_{Hb}-n_{pl})>>1$), we have: $\sigma_{scat}=\sigma_{tot}-\sigma_{abs}=\pi r^2$. So, for this case: $\sigma_{scat}/\sigma_{tot}=\frac{1}{2}$, which means that they are of the same order of magnitude.

Simulations were carried out utilizing various models of multiple scattering theories, such as the model of Twersky, diffusion models (which provide better approximation for blood in a regular situation as compared to that of the model of Twersky), model of Hemenger, model of Rogozkin, and Small-Angle model. The transport theory dealing with average values was also considered in the simulations.

The above models are disclosed, for example, in the following articles:

"Interface Effects in Multiple Scattering by Biological Suspensions", V. Twersky, Journal of the Optical Society of America, Vol. 60, No. 7, pp. 908–914, 1970;

"Optical Properties of Turbid Media with Specularly Reflecting Boundaries: Applications to Biological Problems", R. P. Hemenger, Appl. Opt., Vol. 16. NO.17, 99. 2007–2012, 1997;

"Long-Range Correlations in Wave Reflection from a Disordered Medium", D. B. Rogozkin, Phys. Rev. B. Vol. 51, No. 18, pp. 12256–12267, 1995;

"Long-Range Intensity Correlations for the Multiple Scattering of Waves in Unordered Media", D. B. Rogozkin, JETP Vol. 84(5), pp. 916–939, 1997; and "Intensity Correlation in a Disordered Medium with Large Scaterrers", D. B. Rogozkin, Physics Letters A 178, pp. 431–439, 1993.

Since the transmissions at different wavelengths are the functions of the number of particles in aggregates or particle size, the transmission at one wavelength can be expressed as a parametric function of the transmission at another wavelength. This function is a straight line with reasonable accuracy. This conclusion is verified for both the transmissions themselves and the logarithms of transmission for different models and different simulations of erythrocyte shape.

If the transmission signal $T_1(t)$ is measured when using the incident wavelength $\lambda_1$, and the transmission signal $T_2(t)$ is measured when using the incident wavelength $\lambda_2$, then the slope of the line $T_1(\lambda_1)/T_2(\lambda_2)$ (or log $T_1(\lambda_1)$/log $T_2(\lambda_2)$ is a certain parameter, called "parametric slope" (PS) for a specific patient that can be determined. By this, we can get rid of the explicit usage of the size of aggregates, i.e., the values that cannot be known from experiments in vivo.

The model of Rogoskin for spheres is used to obtain an approximate analytical expression of the parametric slope PS. It should however be noted that, for the cases of more complicated shapes, the proper generalization also may be done.

Thus, the following expression is used:

$$PS = \frac{(\partial T/\partial r)_{\lambda_2}}{(\partial T/\partial r)_{\lambda_1}} = \frac{(\partial T/\partial \mu_{tr})_{\lambda_2}}{(\partial T/\partial \mu_{tr})_{\lambda_1}} \cdot \frac{(\partial \mu_{tr}/\partial r)_{\lambda_2}}{(\partial \mu_{tr}/\partial r)_{\lambda_2}}$$

wherein T is the transmission signal and $\mu_{tr}$ is the transport scattering coefficient that describes the energy decay for the case of anisotropic scattering, and is determined as follows: $\mu_{tr} = \mu_{scat}(1-g)$, g being the anisotropic coefficient.

Here, the case when $(\mu_{diff}*d) \geq 1$ and $\mathrm{Sinh}(\mu_{diff}*d) \approx \exp(\mu_{diff}*d)$ is used, wherein $\mu_{diff}$ is the diffusion coefficient; d is the thickness of the blood slab.

$$(\partial T/\partial \mu_{tr})_\lambda = -<H(\theta,1)> \cdot 3^{1/2} \cdot (\tfrac{1}{2}) \cdot (\mu_{abs}/\mu_{tr}) \cdot [d+(1/\mu_{diff}) \cdot (1+2(\mu_{abs}/\mu_{tr}))] \cdot \exp(-\mu_{diff} \cdot d)$$

At $(\mu_{abs}/\mu_{tr}) \gg 1$, we have:

$$(\partial T/\partial \mu_{tr})_\lambda = -<H(\theta,1)> \cdot (\mu_{abs}/\mu_{tr}) \cdot [3^{1/2} \cdot (\tfrac{1}{2}) \cdot d + (1/\mu_{tr})] \cdot \exp(-3^{1/2} \cdot \mu_{abs} \cdot d)$$

At $(\mu_{abs}/\mu_{tr}) \ll 1$, we have:

$$(\partial T/\partial \mu_{tr})_\lambda = -<H(\theta,1)> \cdot \tfrac{1}{2} \cdot (\mu_{abs}/\mu_{tr}) \cdot [3^{1/2} \cdot d + (1/(\mu_{abs} \cdot \mu_{tr}))^{1/2}] \cdot \exp(-3 \cdot \mu_{abs} \cdot \mu_{tr})_{1/2} \cdot d)$$

Here, $H(\theta,1)$ is the function of Chandrasekhar that depends on the angle $\theta$ of the radiation propagation, $<H(\theta,1)>$ is the value averaged by all angles of radiation propagation.

Analogous, the expressions for derivatives of Log T can be obtained and the parametric slope for Log T can be defined:

$$\partial(\log T)/\partial \mu_{tr})_\lambda = -(\tfrac{3}{2}) \cdot (\mu_{abs}/\mu_{diff}) \cdot [d+(1/\mu_{diff}) \cdot 1 + 2 \cdot \mu_{abs}/\mu_{tr}))]$$

At $(\mu_{abs}/\mu tr) \gg 1$, we have:

$$\partial(\log T)/\partial \mu_{tr})_\lambda = -[(3^{1/2}/2) \cdot d + (1/\mu_{tr})]$$

At $(\mu_{abs}/\mu tr) \ll 1$, we have:

$$\partial(\log T)/\partial \mu_{tr})_\lambda = -(\tfrac{1}{2}) \cdot (\mu_{abs}/\mu_{tr})^{1/2} \cdot [3^{1/2} \cdot d + (1/\mu_{abs} \cdot \mu_{tr})^{1/2}]$$

For the Small-Angle model:

$$\partial(\log T)/\partial \mu_{tr})_\lambda = -(\tfrac{1}{2}) \cdot (\mu_{abs}/\mu_{tr})^{1/2} \cdot d$$

The derivative $(d\mu_{tr}/dr)_\lambda$ is got from the above expression for the scattering coefficient $\mu_{scat}$ for the sphere-based model.

The following expression is known:

$$(\partial \mu_{tr}/\mu r)_\lambda = -(\tfrac{3}{2}) \cdot (1/r^2) \cdot [K(\omega) - \omega \cdot K'(\omega)] \cdot H(1-H) \cdot (1 \cdot g)$$

wherein g is the average cosine of the scattering angle ($g = <\cos \theta>$) and is connected with the anisotropy of the radiation scattering.

In the region of real value of parameters $1 < \omega < 2$, there is the approximation $K(\omega) \approx 0.82053*\omega + 0.0366$. Then, we have:

$$(\partial \mu_{tr}/\partial r)_\lambda = -\tfrac{3}{2}) \cdot (1/r^2) \cdot 0.0366 \cdot H(1-H) \cdot (1-g)$$

The above ratio $(d\mu_{tr}/dr)_\lambda$ depends on the wavelength through the factor $(1-g)$ only.

The value $\mu_{tr}$ with $K(\omega) \approx 0.82053*\omega$ becomes:

$$\mu_{tr} \approx (\tfrac{3}{2}) \cdot 0.82053 \cdot 2 \cdot \pi \cdot (1/\lambda) \cdot H \cdot (1-H) \cdot (1-g)$$

If we substitute this expression in the above equations for $(dT/d\mu_{tr})_\lambda$, we receive the expression that depends on the wavelength very simply and does not depend on the size of particles.

As the result of substitution of $\mu_{tr}$ and $(d\mu_{tr}/dr)_\lambda$ in the above expression for PS, we receive the parameter that does not depend on the particle size.

Now we shall describe how the above theoretical considerations can be used in practice. What we actually obtained through the above simulations, is the fact that there exist a parameter ("parametric slope"), which does not depend on the particle size and only on the concentration of hematocrit in blood. This fact can be used for determining the concentration of a substance of interest in blood.

To do this, first, a set of calibration curves should be provided. Each calibration curve corresponds to a specific substance and is in the form of a parametric slope (PS), as the function of the hematocrit. This can be done by applying two kinds of measurements to a large number of patients. The measurements of one kind are those of the present invention enabling the determination of the parametric slope value for each patient (as will be described below), and the others are conventional ones enabling the determination of the corresponding parameter for the same patient. This set of calibration curves presents reference data, which is previously stored in the memory of the control unit.

Then, for a specific patient, two measurement sessions are applied with the above-described measurement apparatus 1 in vivo (or apparatus 100 in vitro), with two different wavelengths $\lambda_1$ and $\lambda_2$. These wavelengths are selected in accordance with the given task, namely the blood parameter to be determined, as will be exemplified further below. These measurements can be taken within the initial time interval of the entire time period during which the blood flow cessation state is maintained, namely the time interval where the time changes of the transmission signal are stronger as compared to the asymptotic time interval, as well as during the asymptotic time interval.

For example, if the concentration of hemoglobin is to be determined, the two selected wavelengths are those of the absorption of hemoglobin and plasma (water) in the ranges where the difference in the absorption of hemoglobin and water is more sharply expressed, i.e., typically 600–1000 nm and 1100–1400 nm, but may also be 940–980 (water sensitive space) and 600–930 (hemoglobin sensitive space). In the present example, the wavelengths $\lambda_1 = 950$ nm and $\lambda_2 = 1300$ nm are used. The corresponding graphs of the transmission logarithms $\log(T_1)$ and $\log(T_2)$ as the functions of time t corresponding to these wavelengths are shown in FIG. 3a.

Figure 6A:
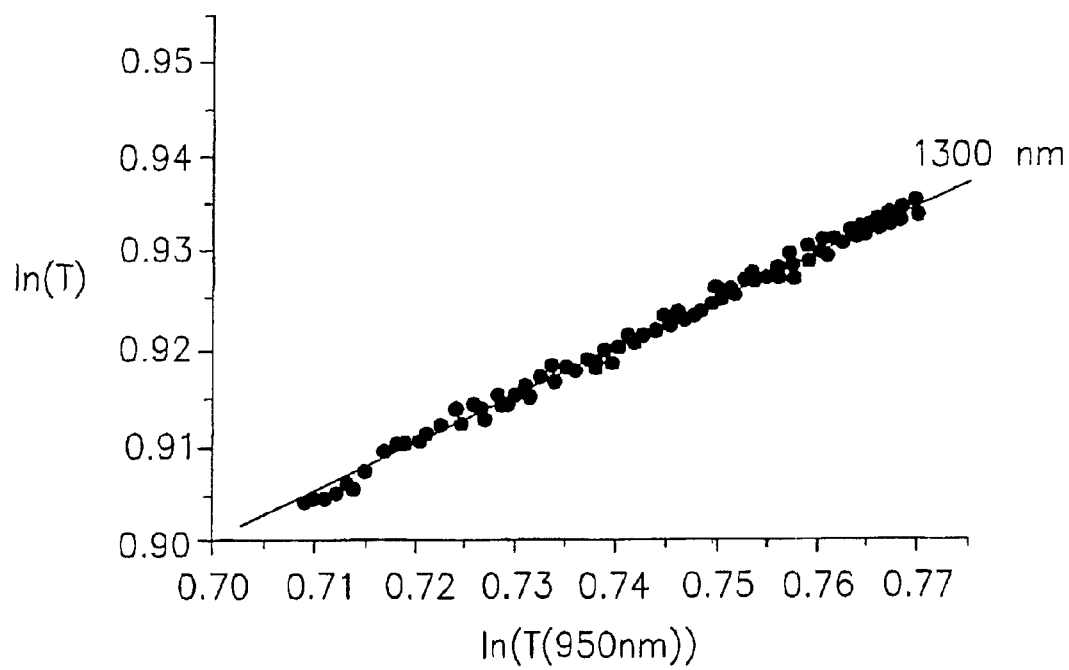
Figure 6B:
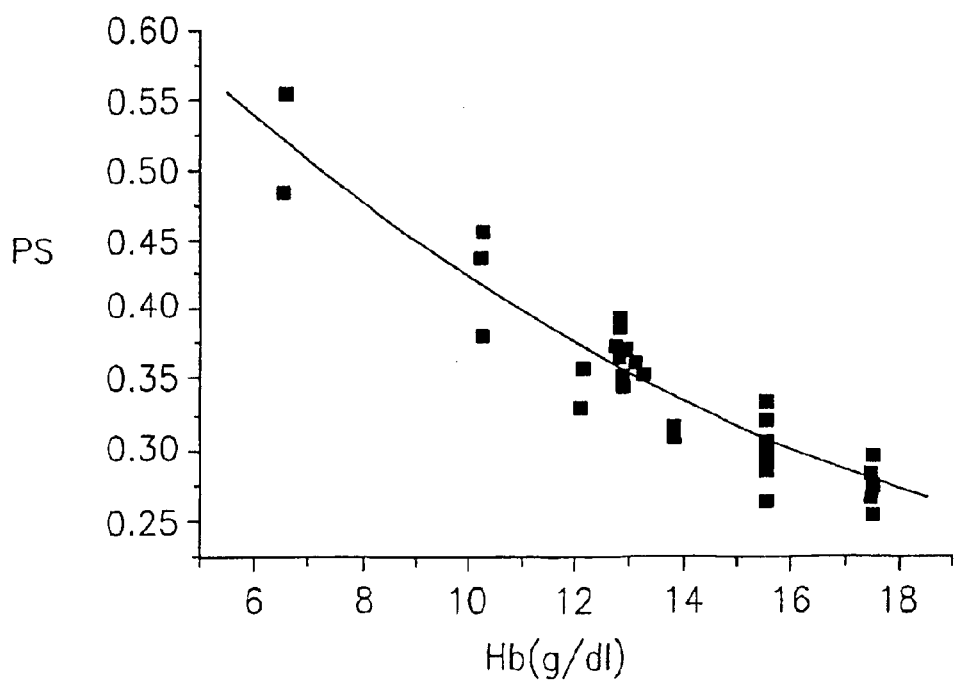

As graphically illustrated in FIG. 6, to determined a parametric slope PS, the function of the transmission logarithm at the wavelength $\lambda_2$, i.e., $\mathrm{Log}(T_2)$, versus the transmission logarithm at the wavelength $\lambda_1$, i.e., $\mathrm{Log}(T_1)$ is determined over the initial time interval. This graph is obtained by the linear regression algorithm. The value of the $\mathrm{tg}(\phi)$ corresponds to the parametric slope PS. The corresponding calibration curve is shown in FIG. 6b. By using this curve, the concentration of hemoglobin can be determined for the specific patient, to whom the measurements are applied.

Figure 7A:
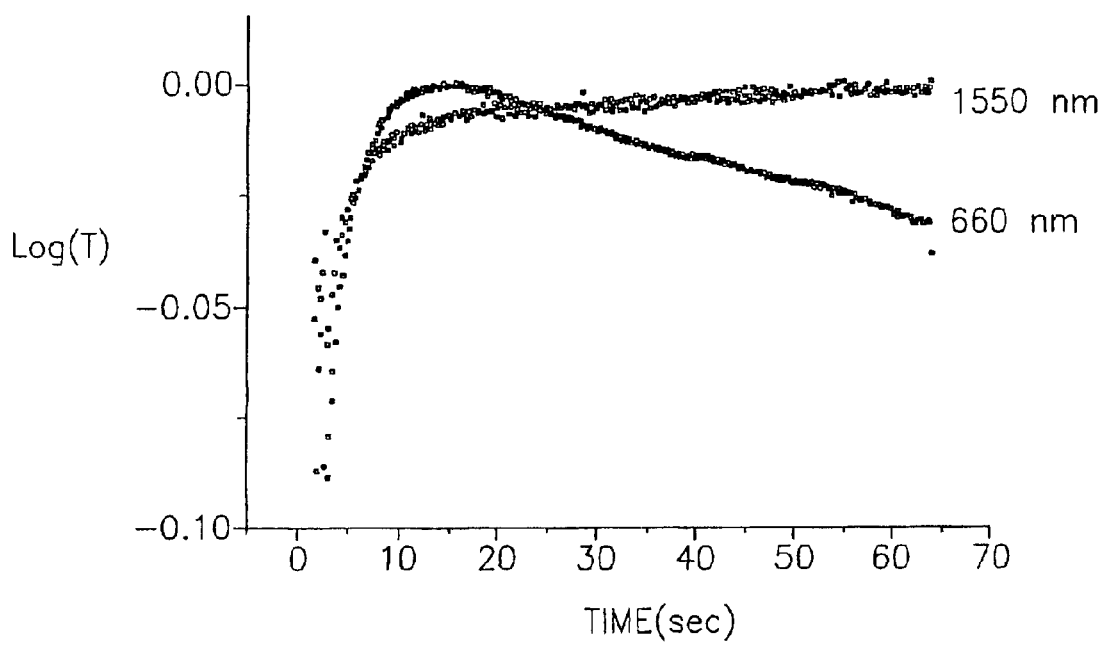
Figure 7B:
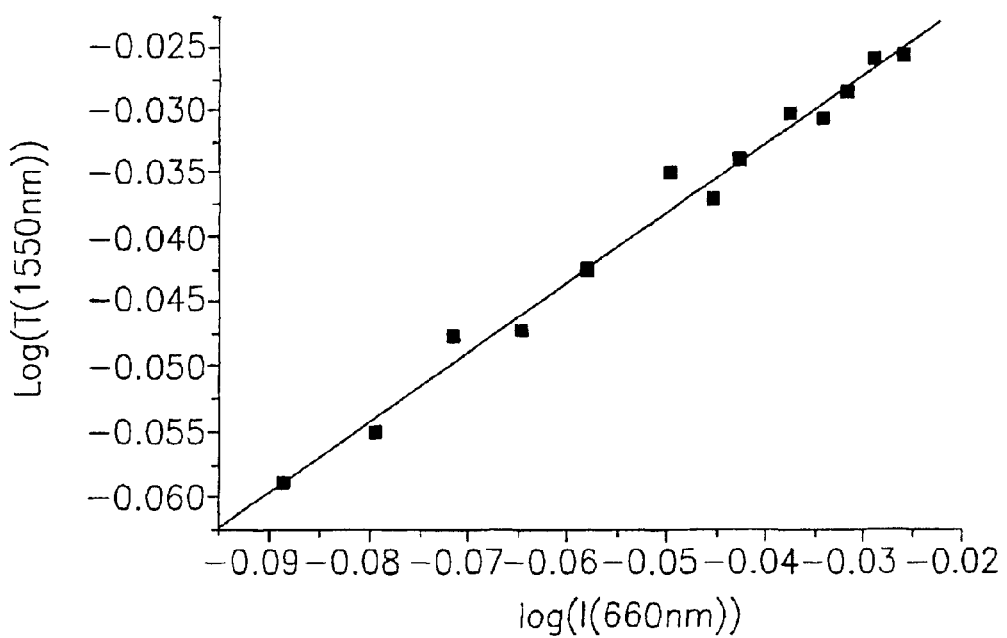

Turning now to FIGS. 7a and 7b, there are illustrated two steps in the method for determining the concentration of glucose. Here, the wavelengths $\lambda_1$ and $\lambda_2$ are selected in the ranges 600–1300 nm and 1500–1600 nm, respectively, namely $\lambda_1 = 660$ nm and $\lambda_2 = 1550$ nm. FIG. 7a illustrates the corresponding transmission signals as the functions of time, i.e., $T_1(t)$ and $T_2(t)$. Then, the function $\log T_2$ vs. $\log T_1$ is determined, as graphically illustrated in FIG. 7b, and the corresponding parametric slope is determined as described above. Having determined the parametric slope value for a specific patient, a corresponding calibration curve (not shown) is used for determining the glucose concentration for this specific patient.

Another important blood parameter that can be determined with the invented method is the oxygen saturation in the patient's blood. Oxygen saturation is defined as the ratio of the content of oxyhemoglobin ($HbO_2$) to the total amount of hemoglobin (Hb) in the blood volume unit. The classic pulse oximetry method allows for determining the oxygen saturation. This method utilizes the so-called "natural pulsatile" component of a light transmission signal. This pure natural pulse-related signal component of a detected signal, determined by an appropriate signal processing technique, is commonly called the "AC component" of the detected signal, whereas the entire transmission signal by itself is called the "DC component" of the detected signal. The transmission measurements in the pulse oximetry are carried out simultaneously at two different wavelengths, for example $\lambda_1=760$ nm and $\lambda_2=940$ nm, where the significant difference in the light absorption of oxyhemoglobin and hemoglobin exists between the two chosen wavelengths. Two pairs of AC and DC components are obtained. Generally, the ratio R, defined as $(AC/DC)_{\lambda 1}/(AC/DC)_{\lambda 2}$, is the value of oxygen saturation.

Figure 8A:
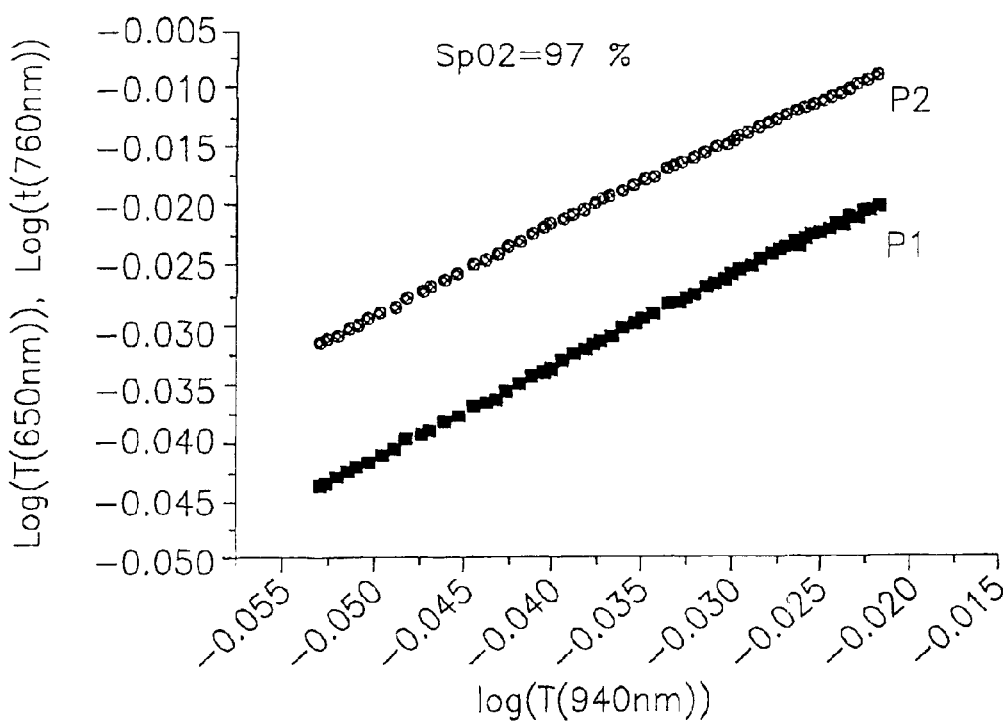

We applied the "parametric slope" concept and obtained the same results as with the pulse oxymetry technique. FIG. 8a illustrates two graphs $P_1$ and $P_2$ (the provision of only one of them being sufficient for the purposes of the present invention), corresponding respectively to (log $T_1)_{\lambda 1}$ vs. (log $T_3)_{\lambda 3}$ and (log $T_2)_{\lambda 2}$ vs. (log $T_3)_{\lambda 3}$. The measured data $T_1(t)$, $T_2(t)$ and $T_3(t)$ is obtained in the above-described manner using the following wavelengths of incident radiation: $\lambda_1=650$ nm, $\lambda_2=760$ nm and $\lambda_3=940$ nm. It should be understood that the use of two wavelengths and, correspondingly, the provision of one parametric slope related graph, is sufficient for the determination of the parametric slope PS.

Generally, a calibration curve to be used for determining the oxygen saturation for a specific patient may be constructed as described above, i.e., applying measurements to various patients. Alternatively, or additionally, in the case of oxygen saturation determination, the calibration curve can be plotted when applying the two kinds of measurements for a single patient in a breath hold experiment using a multiple-occlusion mode. This is illustrated in FIGS. 8b and 8c.

Figure 8B:
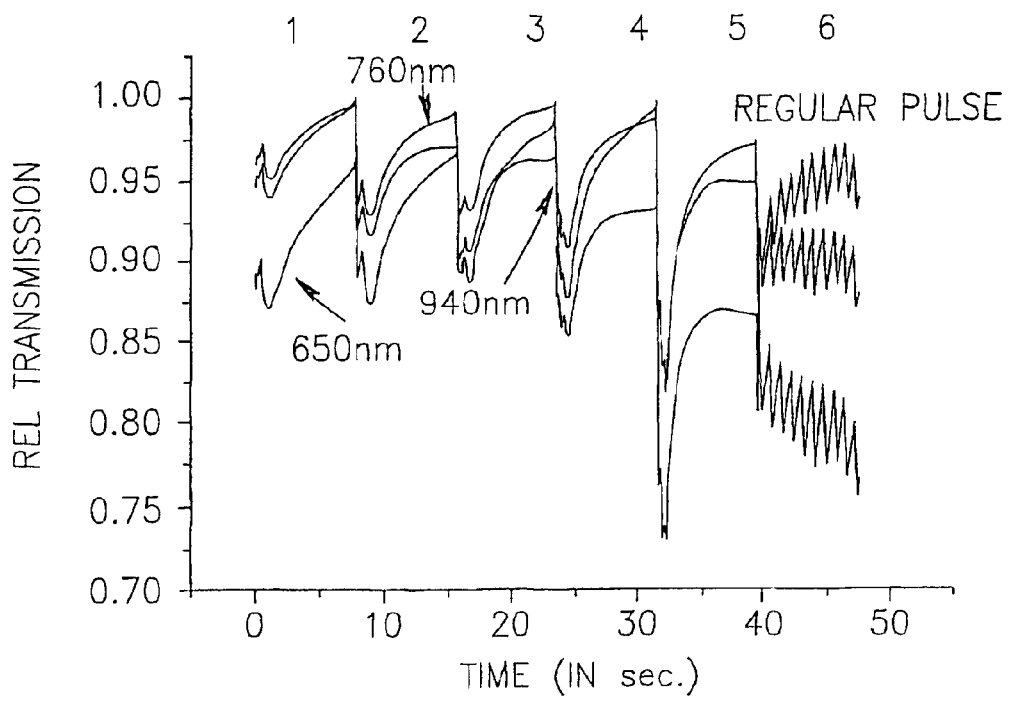
Figure 8C:
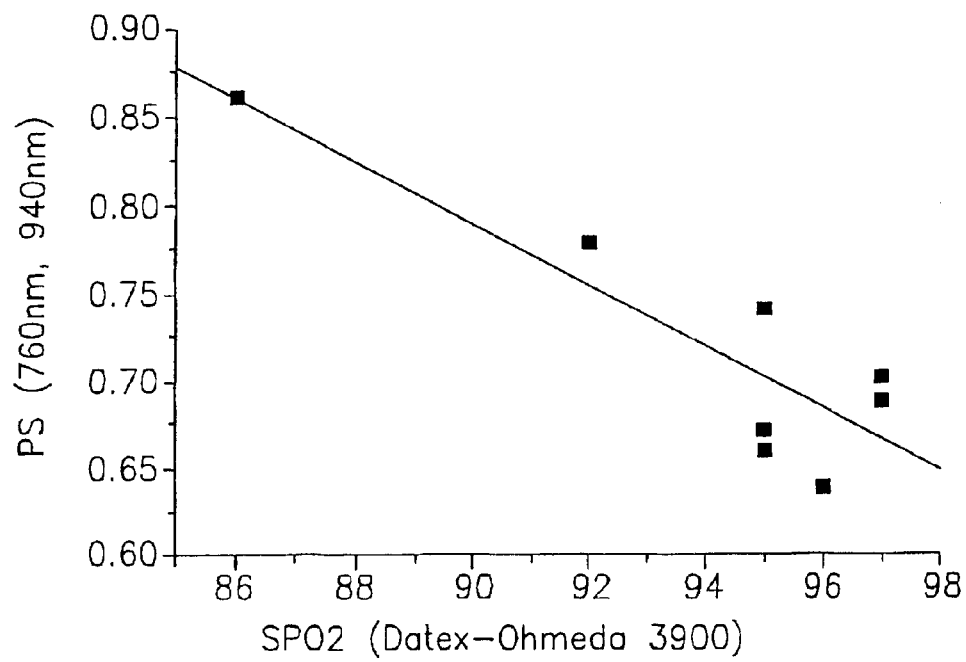

FIG. 8b shows the measured data in the multiple-occlusion mode in the form of the transmission functions $T_1(t)$, $T_2(t)$ and $T_3(t)$ corresponding, respectively, to the wavelengths $\lambda_1=650$ nm, $\lambda_2=760$ nm and $\lambda_3=940$ nm. As shown, several occlusions were performed during the state of the patient's breath hold, and the corresponding parametric slope values were determined during the time interval of the saturation decrease. Concurrently, conventional measurements are applied to the same patient, for example to his other finger, for determining the changes in the oxygen saturation. FIG. 8c shows the so-obtained calibration curve in the form of the parametric slope PS as the function of the oxygen saturation SPO2.

It should be noted, although not specifically shown, that the similar results for the oxygen saturation, as well as for the concentrations of hemoglobin and glucose, were obtained when applying the "parametric slope" based measurements to a blood sample in cuvette, i.e., in vitro measurements.

Figure 9A:
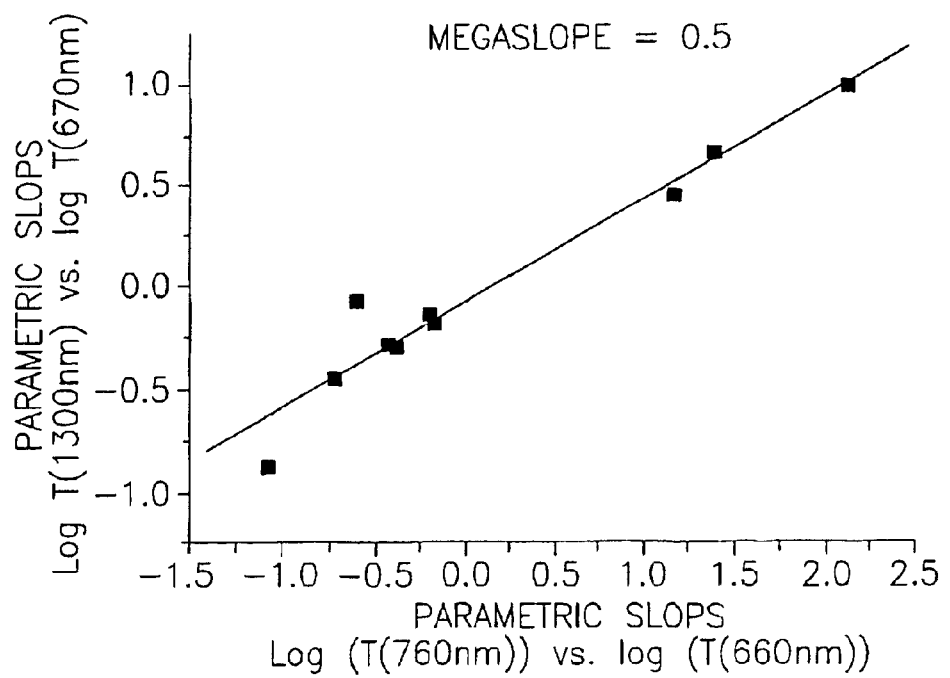
FIGS. 9a and 9b illustrate some more features of the present invention relating to a so-called "MegaSlope" concept, wherein FIG. 9a graphically shows the MegaSlope graph plotted using the measured data of FIG. 3a, and FIG. 9b shows the corresponding calibration curve.
Figure 9B:
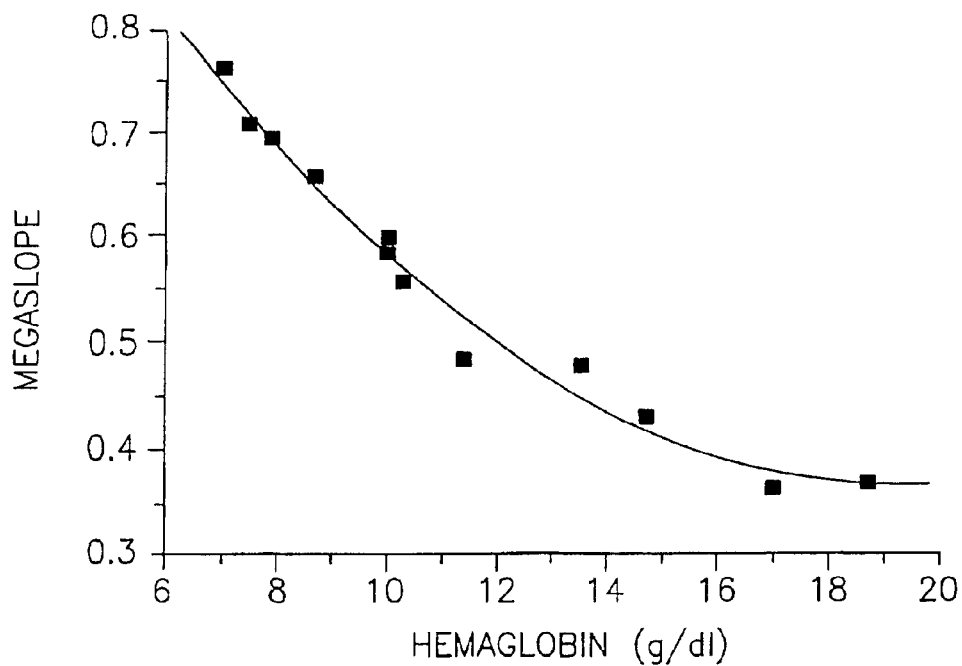

FIGS. 9a and 9b illustrate another important feature of the present invention consisting of the determination of a so-called "MegaSlope" (MS). FIG. 9a shows a graph P' determined from the measured data shown in FIG. 3a. The wavelengths used are: $\lambda_1=660$ nm, $\lambda_2=950$ nm and $\lambda_3=1300$ nm. To this end, the entire time period in FIG. 3a is divided into a plurality of time intervals $\Delta t$—ten in the present example, and for each time interval $\Delta t$ a pair of parametric slope values is obtained from the following: (log $T)_{\lambda 3}$ vs. (log $T)_{\lambda 2}$ and (log $T)_{\lambda 1}$ vs. (log $T)_{\lambda 2}$. In other words, each point in the graph P' corresponds to a pair of parametric slopes calculated for a pair of wavelengths $\lambda_3-\lambda_2$ and $\lambda_1-\lambda_2$, respectively, each for a corresponding one of the time intervals $\Delta t$. Each such parametric slope is determined in the above-described manner. The MegaSlope is determined as tg($\phi$). A calibration curve shown in FIG. 9b presents the MegaSlope as the function of hemoglobin concentration, i.e., MS(H).

Figure 10:
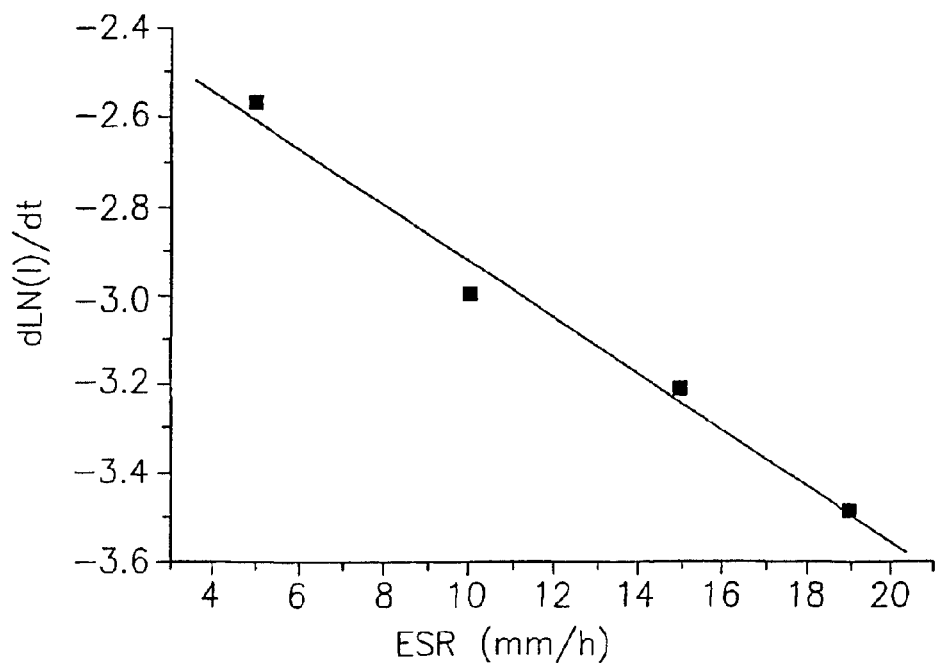
FIG. 10 illustrates the determination of Erythrocyte Aggregation Rate, showing $\Delta(\log T)/\Delta t$ as the function of Erythrocyte Sedimentation Rate, obtained through the conventional in vitro measurements.

One more important feature of the present invention consists of determining the Erythrocyte Aggregation Rate (EAR) for a specific patient. Assuming that the only process that takes place at the state of the blood flow cessation is the erythrocytes' aggregation, the EAR can be simply determined as the rate of the time changes of light response signal, i.e., $\Delta T/\Delta t$ (or $\Delta \log T/\Delta t$). To this end, the transmission as the function of time is measured with one wavelength of incident radiation. For more precise measurements, two such transmission signals as functions of time are measured with two different wavelengths of incident radiation. As for the time interval $\Delta t$, it may be either initial time interval or asymptotic time interval. The EAR parameter can be used for the determination of such an important parameter as Erythrocyte Sedimentation Rate (ESR). This is illustrated in FIG. 10, showing the EAR ($\Delta \log T/\Delta t$) as the function of ESR, the latter being measured in the conventional in vitro manner.

Thus, the advantages of the present invention are self-evident. We have proved that the main effect defining the optical characteristics of blood in the state of temporarily blood flow cessation is the erythrocytes' aggregation. In other words, in the asymptotic time interval, the erythrocyte serves as the sensor for the determination of the various blood parameters. The technique of the present invention, preferably performed in a non-invasive manner, but even in an invasive manner, is simpler and quicker then the conventional one. A physician can apply this technique to evaluate the various blood conditions of a patient, and then, if desired, direct him to a laboratory for more careful measurements. The parameter $x(n_{Hb}-n_{pl})$ can be used in the set of calibration curves for PS and MS or the combination of the both.

What is claimed is:

1. A method of optical measurements of at least one desired parameter of a patient's blood, the method comprising the steps of:

providing a state of blood flow cessation of the patient's blood within a measurement region, and maintaining the blood-flow cessation state during a predetermined time period;

performing measurement sessions within said predetermined time period, each measurement session including at least two measurements with different wavelengths of incident light, and obtaining measured data representative of the time dependence of light response of the blood in the measurement region;

analyzing the measured data for determining said at least one desired parameter, extracted from optical characteristics associated with erythrocytes aggregation process during the state of the blood flow cessation.

2. The method according to claim 1, wherein said state of the blood flow cessation in the measurement region is provided by applying an occlusion mode to the patient's blood perfused fleshy medium.

3. The method according to claim 2, wherein the application of the occlusion mode comprises the application of over-systolic pressure to the patient's blood perfused fleshy medium at a location upstream of said measurements region with respect to the direction of the normal blood flow in the patient's body.

4. The method according to claim 3, and also comprising the step of preliminary optical measurements for detecting the existence of the blood flow cessation state.

5. The method according to claim 2, wherein said predetermined period of time is insufficient for irreversible changes to occur in the fleshy medium.

6. The method according to claim 5, wherein said predetermined period of time is from one second to several minutes.

7. The method according to claim 1, wherein said state of the blood flow cessation in the measurement region is provided by applying an occlusion mode to the flow of the patient's blood sample into a cuvette, said measurement region being located in the cuvette.

8. The method according to claim 1, wherein the analyzing of the measured data comprises the step of:
   determining a Rouleaux Geometry Factor (RGF) characterizing the changes of the light response of blood in the state of blood flow cessation as a function of time and wavelengths of the incident radiation, associated with the erythrocytes' aggregation.

9. The method according to claim 8, wherein the determination of the RGF comprises:
   determining a ratio $\Delta(\log T)/\Delta t$ as a function of wavelength $\lambda$ obtained from several measurement sessions with the different wavelengths, $\Delta t$ being a preset time interval of said predetermined period of time; and
   determining a cut-off wavelength corresponding to the condition where T is the measured light response and $\Delta(\log T)/\Delta t=0$.

10. The method according to claim 9, wherein said preset time interval is an asymptotic time interval characterized by relatively slow changes of the light response signal with time, as compared to an initial time interval of said predetermined period of time.

11. The method according to claim 9, wherein said desired parameter to be determined is an evaluated value of a parameter $(n_{Hb}-n_{pl})$ for said patient, wherein $n_{Hb}$ is the refraction index of hemoglobin in erythrocyte, and $n_{pl}$ is the refraction index of plasma.

12. The method according to claim 11, wherein the evaluation of the parameter $(n_{Hb}-n_{pl})$ comprises the utilization of theoretical data representative of a scattering function $K(x(n_{Hb}-n_{pl}))$, wherein $x=2\pi a/\lambda$, a being the effective size of erythrocyte.

13. The method according to claim 8, wherein the determination of the RGF comprises:
   determining a ratio or $\Delta T/\Delta t$ as a function of wavelength $\lambda$ obtained from several measurement sessions with the different wavelengths, $\Delta t$ being a preset time interval of said predetermined period of time; and
   determining a cut-off wavelength is that corresponding to the condition where T is the measured light response and $\Delta T/\Delta t=0$.

14. The method according to claim 1, wherein the analyzing of the measured data comprises the steps of:
   determining a parametric slope, said at least two wavelengths being selected in accordance with said desired parameter to be determined; and
   using reference data in the form of a calibration curve of the parametric slope as a function of values of the desired parameter.

15. The method according to claim 14, wherein the determination of the parametric slope comprises the determination of a function $T_{\lambda 2}(T_{\lambda 1})$, wherein $T_{\lambda 2}$ and $T_{\lambda 1}$ are the measured data corresponding to the wavelengths $\lambda_2$ and $\lambda_1$ of the incident radiation, respectively, the function $T_{\lambda 2}(T_{\lambda 1})$ being determined for a preset time interval of said predetermined time period.

16. The method according to claim 15, wherein said preset time interval is an initial time interval characterized by relatively strong changes of the light response signal with time, as compared to a next, asymptotic time interval of said predetermined period of time.

17. The method according to claim 15, wherein said preset time interval is an asymptotic time interval characterized by relatively slow changes of the light response signal with time, as compared to an initial time interval of said predetermined period of time.

18. The method according to claim 14, wherein the determination of the parametric slope comprises the determination of a function $\log T_{\lambda 2}(\log T_{\lambda 1})$, wherein $T_{\lambda 2}$ and $T_{\lambda 1}$ are the measured data corresponding to the wavelengths $\lambda_2$ and $\lambda_1$ of the incident radiation, respectively, the function $T_{\lambda 2}(T_{\lambda 1})$ being determined for a preset time interval of said predetermined time period.

19. The method according to 14, wherein said desired parameter is the concentration of a certain substance in blood.

20. The method according to claim 19, wherein said calibration curve is determined from values of the parametric slope and values of the concentration obtained for different patients.

21. The method according to claim 19, wherein said substance is hemoglobin.

22. The method according to claim 21, wherein the at least two selected wavelengths are in the ranges of 600–1000 nm and 1100–1400 nm.

23. The method according to claim 19, wherein said substance is glucose.

24. The method according to claim 23, wherein the at least two selected wavelengths are in the ranges of 1500–1600 nm and 600–1300 nm.

25. The method according to claim 14, wherein said desired parameter is oxygen saturation.

26. The method according to claim 25, wherein said at least two wavelengths are in the ranges of 600–780 nm and 820–980 nm.

27. The method according to claim 25, wherein said calibration curve is determined from values of the parametric slope and values of the oxygen saturation obtained for different patients.

28. The method according to claim 25, wherein said calibration curve is plotted by applying at least two multiple-occlusion measurement sessions with said at least two selected wavelengths to the blood of said patient in the measurement region, determining the parametric slope values for each occlusion, and concurrently determining the oxygen saturation in the blood perfused fleshy medium of said patient outside said measurement region.

29. The method according to claim 1, wherein the analyzing of the measured data comprises the determination of Erythrocyte Aggregation Rate, as $\Delta T/\Delta t$ where T is the measured light response and $\Delta t$ being a preset time interval of said predetermined period of time.

30. The method according to claim 29, wherein $\Delta t$ is within an initial time interval of the predetermined period of time characterized by relatively strong changes of the light response signal with time, as compared to a next, asymptotic time interval of said predetermined period of time.

31. The method according to claim 29, wherein Δt is an asymptotic time interval of the predetermined period of time characterized by relatively slow changes of the light response signal with time, as compared to an initial time interval of said predetermined period of time.

32. A method of optical measurements of desired parameters of a patient's blood extracted from optical characteristics associated with erythrocytes aggregation process during a state of the blood flow cessation, the method comprising the steps of:

providing the state of the blood flow cessation within a measurement region, and maintaining the blood-flow cessation state during a predetermined time period;

performing measurement sessions within said predetermined time period, each measurement session including at least two measurements with different wavelengths of incident light, and obtaining measured data representative of the time dependence of light response of the blood in the measurement region;

analyzing the measured data for determining said at least one desired parameter, by determining at least one parametric slope value and a Rouleaux Geometry Factor (RGF) for said patient, the RGF characterizing the changes of the light response of blood at the state of the blood flow cessation as a function of time and wavelengths of the incident radiation, associated with the erythrocytes' aggregation.

33. A method of optical measurements of at least one desired parameter of blood of a specific patient extracted from optical characteristics associated with erythrocytes aggregation process during a state of the blood flow cessation, the method comprising the steps of:

providing reference data in the form of a function describing diffraction effects on particles, $K(x(n_{Hb}-n_{H2O})$, wherein $x=2\pi a/\lambda$; a is the size of erythrocyte, $n_{Hb}$ is the refraction index of hemoglobin and $n_{pl}$ is the refraction index of water, $\lambda$ is the wavelength of incident radiation;

providing the state of the blood flow cessation and maintaining said state during a predetermined period of time;

performing measurement sessions within said predetermined time period, each measurement session including several measurements with different wavelengths of incident radiation, and obtaining measured data representative of the time dependence of light response signals;

analyzing the measured data for determining a Rouleaux Geometry Factor (RGF) for the specific patient, the RGF characterizing the changes of the light response of blood at the state of the blood flow cessation as a function of time and wavelengths of the incident radiation, associated with the erythrocytes' aggregation.

34. A method of optical measurements of at least one desired parameter of blood of a specific patient extracted from optical characteristics associated with erythrocytes aggregation process during the state of the blood flow cessation, the method comprising the steps of:

providing reference data in the form of at least one calibration curve corresponding to a parametric slope as a function of values of said desired parameter;

providing the state of the blood flow cessation within a measurement region, and maintaining the blood-flow cessation state during a predetermined time period;

performing timely separated measurement sessions within said predetermined time period, each measurement session including at least two measurements with different wavelengths of incident light, and obtaining the time dependence of transmission signals, wherein the at least two wavelengths are selected in accordance with the desired parameter to be determined;

analyzing the obtained data for determining the parametric slope value for said specific patient;

using said calibration curve for determining the value of said desired parameter for said specific patient.

35. A measurement apparatus for performing optical measurements of at least one desired parameter of the patient's blood, the apparatus comprising:

an occlusion assembly operable to apply pressure to a location on a blood containing medium and maintain said pressure for a predetermined time period;

illumination/detection assembly operable for applying optical measurements with at least two different wavelengths of incident radiation to a measurement region in the medium, and generating data representative of light response signals from the measurement region; and a control unit for operating the occlusion and illumination/detection assemblies to allow application of the optical measurements during said predetermined time period, for processing the generated data to determine measured data in the form of at least two time variations of the light response signals corresponding to said at least two wavelengths, respectively, and for analyzing the measured data to determine the at least one desired parameter of the patient's blood;

the apparatus being characterized in that:

the occlusion assembly is applicable to a first location on the medium upstream of a second location that contains said measurement region, with respect to the blood flow direction in the medium, the application of the pressure to the first location resulting in creation of a state of temporary blood flow cessation in the measurement region thereby causing a Rouleaux effect at the state of blood flow cessation;

the control unit comprises:

a memory for storing reference data in the form of a calibration curve of a value of a certain parameter associated with the Rouleaux effect as a function of values of the desired blood parameter;

a processor operable to analyze the measured data in the form of the two time variations to calculate a value of said parameter associated with the Rouleaux effect, and to utilize the reference data to determine the value of the desired parameter of the patient's blood, the analyzing of the measured data from within a preset time interval of said predetermined period of time utilizing optical characteristics of blood associated with the erythrocytes aggregation process during the state of the blood flow cessation.

36. A method of optical measurements of at least one desired parameter of a patient's blood, the method comprising the steps of:

providing a flow of the patient's blood sample into a cuvette;

applying a pressure to a location upstream of the cuvette with respect to the direction of the blood flow, to create a state of blood flow cessation in a measurement region inside the cuvette, and maintaining the blood-flow cessation state during a predetermined time period, the creation of the state of the blood flow cessation in the measurement region causing a Rouleaux effect;

applying optical measurement sessions to said measurement region within said predetermine time period, each measurement session including at least two measurements with different wavelengths of incident light, detecting light response signals from the measurement region, and obtaining measured data in the form of at least two time variations of the light response signals corresponding to said at least two wavelengths, respectively, said variation being caused by the Rouleaux effect;

analyzing the measured data to calculate a value of a certain parameter associated with the Rouleaux effect as a function of time and wavelength of the incident radiation;

utilizing the calculated value of said parameter associated with the Rouleaux effect and utilizing predetermined reference data in the form of a calibration curve of a value of said parameter associated with the Rouleaux effect as a function of values of the desired blood parameter, and determining the desired parameter of the patient's blood.

* * * * *